(12) United States Patent
Tracey et al.

(10) Patent No.: US 11,278,469 B2
(45) Date of Patent: Mar. 22, 2022

(54) BIOELECTRONIC PHARMACEUTICALS

(71) Applicant: THE FEINSTEIN INSTITUTES FOR MEDICAL RESEARCH, Manhasset, NY (US)

(72) Inventors: Kevin J. Tracey, Old Greenwich, CT (US); Sangeeta S. Chavan, Syosset, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 369 days.

(21) Appl. No.: 15/677,062

(22) Filed: Aug. 15, 2017

(65) Prior Publication Data

US 2018/0021214 A1 Jan. 25, 2018

Related U.S. Application Data

(63) Continuation-in-part of application No. PCT/US2016/018569, filed on Feb. 19, 2016.
(Continued)

(51) Int. Cl.
*A61H 23/00* (2006.01)
*A61H 23/02* (2006.01)
(Continued)

(52) U.S. Cl.
CPC ......... *A61H 23/00* (2013.01); *A61H 23/0236* (2013.01); *A61N 1/05* (2013.01);
(Continued)

(58) Field of Classification Search
CPC ............ A61B 5/04001; A61B 5/14532; A61H 23/00; A61H 23/0236; A61H 2230/08; A61H 2230/085; A61N 1/05
See application file for complete search history.

(56) References Cited

U.S. PATENT DOCUMENTS 4,750,499 A * 6/1988 Hoffer ................. A61B 5/1106
607/116
8,855,767 B2 * 10/2014 Faltys .................... A61N 1/375
607/33
(Continued)

FOREIGN PATENT DOCUMENTS

WO 2014169145 A1 10/2014
WO 2016134199 A1 8/2016

OTHER PUBLICATIONS

Communication Supplementary Partial European Search Report dated Nov. 19, 2018 in connection with European Patent Application No. 16753096.3, 8 pages.
(Continued)

*Primary Examiner* — Tu A Vo
*Assistant Examiner* — Alexander Morales
(74) *Attorney, Agent, or Firm* — Amster, Rothstein & Ebenstein LLP

(57) ABSTRACT

Methods are disclosed for treating a subject having a disease or disorder comprising providing the subject with an acoustic energy stimulus derived from a disease-specific, condition-specific, endogenous mediator-specific or pharmacologic agent-specific neurogram in an amount and manner effective to treat the disease or disorder.

20 Claims, 23 Drawing Sheets

Related U.S. Application Data

(60) Provisional application No. 62/237,056, filed on Oct. 5, 2015, provisional application No. 62/118,756, filed on Feb. 20, 2015.

(51) Int. Cl.
  *A61N 1/05* (2006.01)
  *A61B 5/145* (2006.01)
  *A61B 5/24* (2021.01)

(52) U.S. Cl.
  CPC ............ *A61B 5/14532* (2013.01); *A61B 5/24* (2021.01); *A61H 2230/08* (2013.01); *A61H 2230/085* (2013.01)

(56) References Cited

U.S. PATENT DOCUMENTS

| | | | |
|---|---|---|---|
| 10,507,327 B2 | 12/2019 | Tracey et al. | |
| 2004/0015204 A1* | 1/2004 | Whitehurst | A61N 1/37252 607/48 |
| 2007/0027484 A1 | 2/2007 | Guzman et al. | |
| 2009/0247934 A1 | 10/2009 | Tracey et al. | |
| 2010/0049281 A1* | 2/2010 | Libbus | A61B 5/24 607/62 |
| 2011/0118810 A1 | 5/2011 | Cowan et al. | |
| 2011/0150924 A1* | 6/2011 | Della Rocca | A61N 1/306 424/204.1 |
| 2011/0319969 A1 | 12/2011 | Dobak, III | |
| 2012/0316801 A1* | 12/2012 | Rieger | G06N 7/06 702/57 |
| 2014/0228900 A1* | 8/2014 | Osorio | A61N 1/36082 607/3 |
| 2014/0294187 A1* | 10/2014 | Choi | H04R 25/70 381/60 |
| 2014/0294188 A1* | 10/2014 | Rini | H04R 25/70 381/60 |

OTHER PUBLICATIONS

Steinberg B E et al., entitled "Pro- and Anti-inflammatory Cytokines Differentially Activate the Sensory Vagus Nerve," Abstract, Oct. 14, 2014, 1 page, retrieved from the internet: http://www.asaabstracts.com/strands/asaabstracts/abstract.htm?year=2014&index=10&absnum=4244.

Cambridge Electronics Design Limited: "Spike2 for Windows," Jan. 1, 2017, retrieved from the internet: http://ced.co.uk/img/Spike7.pdf, 328 pages [retrieved on Oct. 25, 2018].

PCT International Search Report and Written Opinion dated May 12, 2016 for PCT International Patent Application No. PCT/US2016/18569, 12 pages.

Steinberg B E et al., entitled "Pro- and Anti-inflammatory Cytokines Differentially Activate the Sensory Vagus Nerve," American Society of Anesthesiologists, Abstract, Oct. 14, 2014, 1 page.

Andersson U et al., entitled "Reflex Principles of Immunological Homeostasis," Annu. Rev. Immunol., 2012, 30:313-35, Epub Jan. 6, 2012.

Andersson U et al., entitled "Neural reflexes in inflammation and immunity," J. Exp. Med. vol. 209, No. 6, pp. 1057-1068, 2012.

Borovikova L V et al., entitled "Vagus nerve stimulation attenuates the systemic inflammatory response to endotoxin," Nature, vol. 405, May 25, 2000, pp. 458-462.

Famm K et al., entitled "A jump-start for electroceuticals," Nature, vol. 496, Apr. 11, 2013, pp. 159-161.

Koopman F A entitled "Vague nerve stimulation inhibits cytokine production and attenuates disease severity in rheumatoid arthritis," PNAS, vol. 113, No. 29, 8284-8289, doi: 10.1073/pnas.1605635113, www.pnas.org/cgi/doi/10.1073/pnas.1605635113. Epub Jul. 5, 2016.

Olofsson P S et al., entitled "Single-Pulse and Unidirectional Electrical Activation of the Cervical Vagus Nerve Reduces Tumor Necrosis Factor in Endotoxemia," Bioelectron Med 2:37-42, 2015, pp. 37-42.

Behar M, entitled "Can the Nervous System Be Hacked?" The New York Times Magazine, The Health Issue, May 25, 2014, 7 pages.

Examination report for Australian Patent Application No. 2016219949, dated Dec. 3, 2019.

* cited by examiner

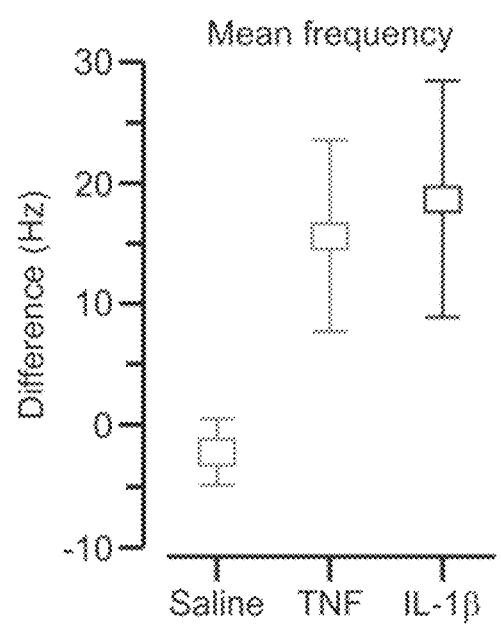
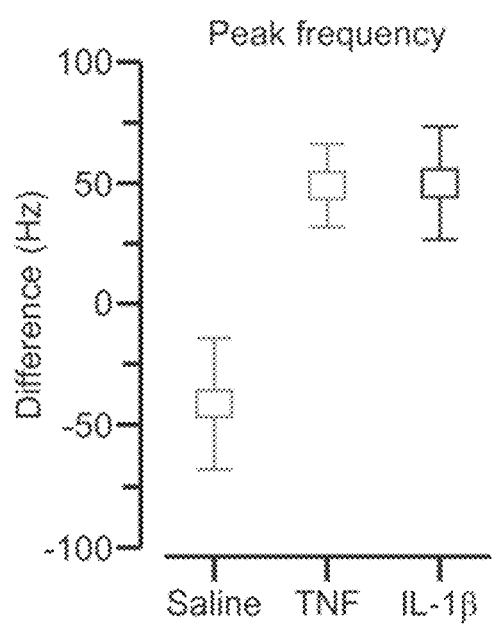
FIG. 4A
FIG. 4B
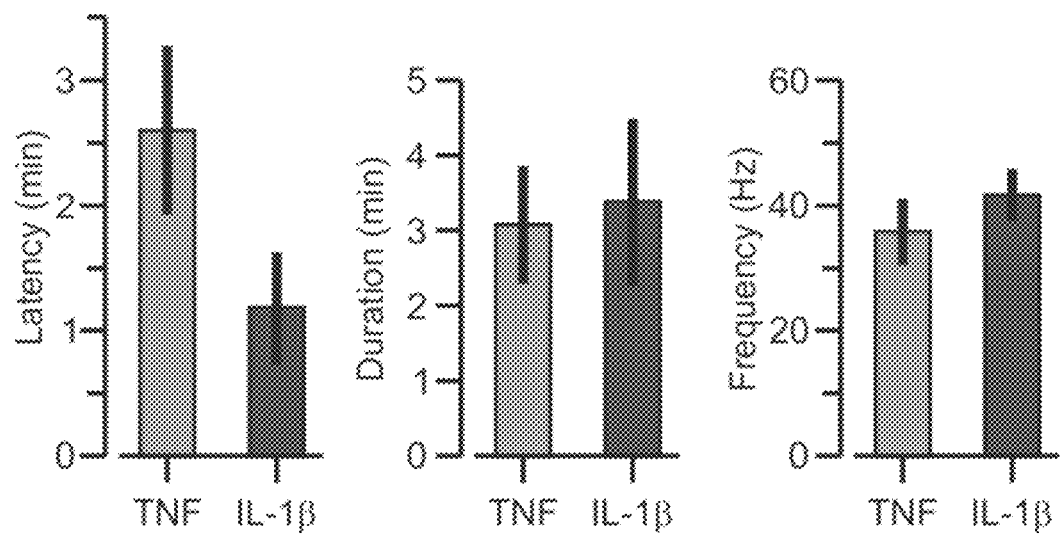
FIG. 4C

BIOELECTRONIC PHARMACEUTICALS

CROSS-REFERENCE TO RELATED APPLICATIONS

This application is a continuation-in-part of and claims priority of PCT International Patent Application No. PCT/US2016/018569, filed Feb. 19, 2016, which designates the United States of America and which claims the benefit of U.S. Provisional Patent Application No. 62/118,756, filed on Feb. 20, 2015, and of U.S. Provisional Patent Application No. 62/237,056, filed on Oct. 5, 2015, the contents of which are herein incorporated by reference into the subject application.

STATEMENT OF GOVERNMENT SUPPORT

This invention was made with government support under grant number W911NF-09-1-0125 awarded by the Defense Advanced Research Projects Agency (DARPA). The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

The nervous system developed over evolutionary time to optimize survival in response to signals from the internal and external environment. In mammals, chemical, mechanical, and electromagnetic signals are sensed by neurons, which propagate action potentials to the central nervous system (CNS). These comprise the afferent arcs of reflex circuits that maintain the body's homeostasis. This fundamental principle of sensing environmental changes in order to mount appropriate reflex responses is central to the physiological mechanisms that allow for not only homeostasis but adaptability and species survival.

Thirty years ago, it was discovered that products of the immune system, including cytokines and other mediators, could be sensed by the nervous system, prompting the suggestion that the immune system could serve as a functional sensory modality (1). In this context, foreign invaders, microbial products, and other exogenous immune stimulators culminate in the release of cytokines. These immune products can in turn interact with the peripheral nervous system and the CNS to elicit neurophysiological responses; however, the question remains whether the sensory neural signals are encoded in cytokine-specific patterns.

There has been an expanding body of knowledge delineating the extensive interface between the nervous and immune systems. Similar to the neural control of the body's general physiological and metabolic states, systemic inflammatory pathways can be modulated by the CNS, with the archetypal pathway being the inflammatory reflex of the vagus nerve (VN) (2). In its efferent arc, electrical signals move down the vagus nerve to the celiac ganglion from which the splenic nerve further propagates the signal towards the spleen. Within the spleen, a specialized subset of T lymphocytes completes the link between the nervous and immune systems (3, 4). Acetylcholine, which is released by these T cells, down-regulates cytokine production by resident macrophage thereby producing a systemic anti-inflammatory effect (3).

In contrast to the well-mapped motor arc, the afferent arc remains incompletely understood. Notably, the vagus nerve is primarily sensory, such that numerous afferent signals regarding physiological status travel the vagus nerve from the periphery into the CNS. Oftentimes neglected is the notion that these signals might include the inflammatory status of the animal. The pioneering work by Niijima and collaborators (5-7) led them to postulate that IL-1β might activate peripheral afferents of the vagus nerve that would signal to the CNS about the presence of this cytokine. Physiological studies have shown that an intact vagus nerve is required for a pyrexia response to intra-abdominal IL-1β administration, further corroborating the notion that the vagus nerve might be a primary peripheral inflammation sensor for the CNS (8, 9). Parallel studies in isolated sensory neurons show that neurons express a variety of cytokine receptors, such as the TNF and IL-1β receptors, and are able to change their activation thresholds when exposed to the corresponding exogenous cytokines (10-12). In combination, these studies suggest that the vagus nerve is an important substrate for a peripheral neural network capable of capturing real-time signals pertaining to changes in peripheral inflammatory and immune states.

The present invention addresses the need for improved methods for treating diseases and disorders, in particular methods that do not require administration of drugs to a subject. The methods disclosed herein use a stimulus pattern derived from a disease-specific or condition-specific or endogenous mediator-specific or pharmacologic agent-specific vagus nerve neurogram to produce an acoustic stimulus pattern that is used to treat the disease or disorder.

SUMMARY OF THE INVENTION

The present invention provides methods for treating a subject having a disease or disorder comprising providing the subject with acoustic energy stimulus derived from a disease-specific or condition-specific or endogenous mediator-specific or pharmacologic agent-specific neurogram in an amount and manner effective to treat the disease or disorder.

As an example, the invention provides methods for controlling blood glucose levels in subjects comprising providing the subject with an acoustic energy stimulus derived from a hypoglycemic- or hyperglycemic-specific vagus neurogram in an amount and manner effective to control blood glucose levels in a subject.

Also provided are methods for generating a corrective stimulus for the treatment of a disease or condition, comprising the steps of: providing a disease-specific, condition-specific, endogenous mediator-specific or pharmacologic agent-specific neurogram, and generating a corrective acoustic energy stimulus based therefrom.

BRIEF DESCRIPTION OF THE DRAWINGS

FIG. 4A-4C. Time domain analysis of TNF and IL-1β mediated neurograms. (A) Boxplot showing the difference (post-injection minus pre-injection) in mean CAP frequency. For TNF (N=6) and saline (N=5), 10-min intervals were used. For IL-1β (N=8), 5-min intervals were used. (B) Boxplot showing the difference in peak CAP frequency. (C) Left, graph depicting the latency (mean±SEM) for the TNF and IL-1β responses. The former is mildly slower than the latter (P=0.043, t test). Middle, graph showing the duration (mean±SEM) of the neurograms induced by TNF and IL-1β. Right, graph presenting the CAP frequency (mean±SEM) of the TNF and IL-1β responses.

DETAILED DESCRIPTION OF THE INVENTION

Figure 1A:
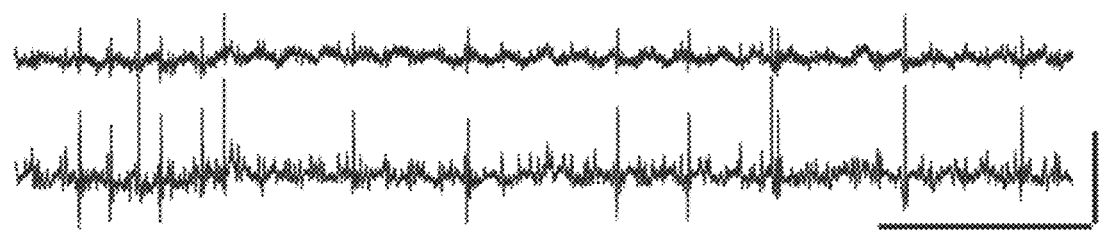
FIG. 1A-1E. Recording vagus nerve compound action potentials. (A) Simultaneous recordings (2 of 3 electrodes are shown) of spontaneous activity in the vagus nerve (VN). (B) Vagus nerve excitation by KCl (4 mM, gray box) applied to the surgical field. Period of quiescent activity before KCl (marked by i) and period of intense spiking during KCl (marked by ii). (C) Identification of compound action potentials using adaptive thresholding. Top, period of quiescent activity before KCl (marked by i). Middle, period of intense spiking during KCl (marked by ii). Line indicates the adaptive threshold used to detect compound action potentials (CAPs). Bottom, identified CAPs are aligned with the trace above. (D) Inset, evoked CAPs are obtained by brief electrical pulses that stimulate the vagus nerve. The graph shows the CAP area (mean±SD), which becomes larger with increasing stimulation intensity (pre-lidocaine circles). Lidocaine (2%) largely blocks the evoked CAPs (post-lidocaine circles). (E) Inset, evoked CAPs previous to treatment with tetrodotoxin (TTX, 100 μM). The graph shows the CAP area (mean±SD) which is completely blocked by the drug. Scale bars (x, y), A, 100 ms, 100 μV; B, 1 sec, 20 μV; C 10 ms, 20 μV.

The present invention provides a method for treating a subject having a disease or disorder comprising providing the subject with an acoustic energy stimulus derived from a disease-specific or condition-specific or endogenous mediator-specific or pharmacologic agent-specific neurogram in an amount and manner effective to treat the disease or disorder.

Also provided is a method for generating a corrective stimulus for the treatment of a disease or condition, comprising the steps of:

providing a disease-specific, condition-specific, endogenous mediator-specific or pharmacologic agent-specific neurogram, and generating a corrective acoustic energy stimulus based therefrom.

The disease or disorder can be, for example, one or more of inflammation, type 1 diabetes, type 2 diabetes, metabolic syndrome, insulin resistance, glucose intolerance, hyperglycemia, hypoglycemia, trauma, bleeding, hemorrhagic shock, ischemia-reperfusion injury, nausea, vomiting, cancer, prostate cancer, arthritis, rheumatoid arthritis, sepsis, endotoxemia, colitis, pancreatitis, inflammatory bowel disease, Crohn's Disease, fever, anorexia, pain, swelling, kidney failure, liver disease, hypothyroidism, a host response to infection, an immune response, and a disease or disorder in which it is desirable to increase the activity or level of a cytokine.

Preferably, an acoustic energy stimulus derived from a cytokine-specific neurogram can be used to modulate a cytokine-specific physiological effect. Preferably, a corrective stimulus pattern derived from a subject's glucose or insulin level can be used to control glucose, and thus can preferably replace administration of insulin to the subject.

The present invention provides a method for controlling blood glucose levels in a subject comprising providing the subject with an acoustic energy stimulus derived from a hypoglycemic- or hyperglycemic-specific neurogram recorded from a vagus nerve in an amount and manner effective to control blood glucose levels in a subject.

In one embodiment, the method is for increasing blood glucose levels in a subject, where the method comprises providing the subject with an acoustic energy stimulus derived from a hypoglycemic-specific, insulin-specific or cortisol-specific neurogram recorded from a vagus nerve in an amount and manner effective to increase blood glucose levels in a subject. The hypoglycemic-specific neurogram can be recorded from a vagus nerve of a subject following, for example, administration of insulin or cortisol to the subject. The subject receiving the acoustic energy stimulus can have, for example, one or more of hypoglycemia, kidney failure, liver disease and hypothyroidism.

In another embodiment, the method is for decreasing blood glucose levels in a subject, where the method comprises providing the subject with an acoustic energy stimulus derived from a hyperglycemic-specific or glucose-specific neurogram recorded from a vagus nerve in an amount and manner effective to decrease blood glucose levels in a subject. The hyperglycemic-specific neurogram can be recorded from a vagus nerve of a subject following, for example, administration of glucose to the subject. The subject receiving the acoustic energy stimulus can have, for example, one or more of diabetes mellitus type 1, diabetes mellitus type 2, metabolic syndrome, insulin resistance, glucose intolerance and hyperglycemia.

In one embodiment, the subject receiving the acoustic energy stimulus has inflammation and the acoustic energy stimulus is derived from an anti-inflammatory-specific neurogram recorded from a vagus nerve. The anti-inflammatory-specific neurogram can be, for example, a dexamethasone-specific neurogram or a cortisol-specific neurogram. Preferable, the acoustic energy stimulus is effective to reduce serum levels of tumor necrosis factor (TNF) in a subject receiving the acoustic energy stimulus.

Electrical sampling of neural activity ("neurograms") can be obtained in human or non-human subjects, such as an animal model of a disease or disorder, wherein the neurograms are disease-specific, condition-specific, endogenous mediator-specific or pharmacologic agent-specific neurograms.

The neurogram can be obtained, for example, in response to administration of physiologically occurring substances to a subject, such as for example, in response to administration of a cytokine. The cytokine can be, for example, a chemokine, a colony stimulating factor, high-mobility group protein B1 (HMGB1), an interferon (IFN), an interleukin (e.g., any of IL-1 through IL-36), a lymphokine, macrophage migration inhibitory factor (MIF), a monokine, a transforming growth factor beta (e.g., TGF-β1, TGF-β2 and TGF-β3), a tumor necrosis factor (e.g., TNFα or TNFβ). The neurogram can be obtained, for example, in response to administration of glucagon, glucose or insulin, or in response to a change in glucose levels, e.g. blood glucose levels. The neurogram can, for example, be recorded in response to a pro-inflammatory signal or an anti-inflammatory signal.

The neurogram can be obtained, for example, from a parasympathetic nerve, a sympathetic nerve, a cranial nerve or a somatic nerve, including, for example, the vagus nerve, splenic nerve, splanchnic nerve, sciatic nerve, or a nerve to a specific organ, such as for example the spleen or liver, or portion of an organ.

Electrical sampling of vagal neural activity ("neurograms") can be obtained from an animal model or a human patient and is preferably obtained from a cervical vagus nerve.

Nerve recording can be carried out using, for example, an implantable electrode, such as, for example, a cuff-style electrode. The neurograms can be obtained from the same subject that is being treated with acoustic stimulation or from a different subject. The subject being treated can be a human subject or a veterinary subject.

The nerve recording signal can be converted to an acoustical energy stimulus, for example, as a .wav file, using for example a program from commercially available Spike 2 software (Cambridge Electronic Design Limited). One can select the window of time of the nerve recording signal and convert that portion of the signal to a .wav file. Preferably, a carrier frequency can be adjusted according to the hearing range of the subject being treated (20, 21). For example, the hearing range in humans is approximately 32 Hz to 20 kHz at 60 dB sound pressure level, and roughly 250 Hz to 8 kHz at 10 dB (20).

Acoustical energy stimulus can be applied to one ear or to both ears of the subject, including, for example, using headphones. Acoustic energy stimulus can include auditory and vibratory energy stimulation.

Also provided, for example, is the use of a hypoglycemic- or hyperglycemic-specific vagus nerve neurogram for providing a subject with an acoustic energy stimulus in an amount and manner effective to treat hypoglycemia or hyperglycemia.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1. Cytokine-Specific Neurograms Recorded from the Afferent Vagus Nerve

Overview

Neural networks in the periphery send signals about the body's physiological state to the central nervous system (CNS) through afferent fibers, and particularly through the vagus nerve (VN). As part of this network, the sensory vagus nerve responds to interleukin-1β (IL-1β) and lipopolysaccharide, and relays these signals to the nucleus tractus solitarius within the CNS. The present study mapped the peripheral neural activity that occurred in response to tumor necrosis factor (TNF) and IL-1β by recording from the cervical vagus nerve of adult mice. With the use of selective surgical vagotomies, the neurograms generated by cytokines were shown to be carried by the afferent fibers of the vagus nerve. Low doses of cytokines (5 µg TNF or 35 ng IL-1β) did not enhance baseline activity of the vagus nerve, whereas higher doses (50 µg TNF or 350 ng IL-1β) triggered significant enhancements. Analysis of temporal dynamics and power spectral characteristics of neurograms mediated by TNF and IL-1β revealed cytokine-selective signals in the vagus nerve.

Materials and Methods

Animals.

All experimental protocols were approved by the Institutional Animal Care and Use Committee (IACUC) at the Feinstein Institute for Medical Research, Northwell Health (formerly the North Shore-LIJ Health System), which follows the NIH guidelines for ethical treatment of animals. The studies used male BALB/c mice (8-12 weeks, weighing 20-30 g), which were purchased from The Jackson Laboratory (Bar Harbor, Me.). They were housed at 25° C., with ad libitum water and chow, and acclimated to a 12-h light and dark cycle for >3 days prior to conducting experiments.

Chemicals.

Lidocaine, tetrodotoxin (Sigma-Aldrich), and human IL-1β (eBiosciences) were purchased. Recombinant and tag-free human TNF was produced in-house. Following expression in *E. coli*, TNF was purified using a cation exchange column and endotoxins removed by phase separation with Triton X-114.

In Vivo VN Recordings.

Mice were fasted (3-4 h) prior to each experiment. Each was induced (isoflurane at 2.5%) and maintained (isoflurane at 1.5%) in the supine position for surgery. A midline cervical incision was made and the left cervical branch of the vagus nerve isolated from the accompanying carotid bundle. Under magnification, the connective tissue was mechanically removed, and the vagus nerve was placed over three custom-built silver hook electrodes. Electrophysiological signals were digitized (sampling rate, 32 kHz) through a data acquisition system (Digital Lynx 4SX, Cheetah v5 software, Neuralynx, Bozeman, Mont.) and referenced to an animal ground electrode placed between the skin and right salivary gland. In all experiments, the vagus nerve was protected from desiccation and insulated by bathing the surgical field with mineral oil. Following acquisition of baseline activity (15-20 min), animals were i.p. injected with TNF, IL-1β, or saline control and recordings were continued for 20-30 min post-injection. The experimenter was grounded whenever manipulating the animal during recordings.

Vagotomies.

Figure 2A:
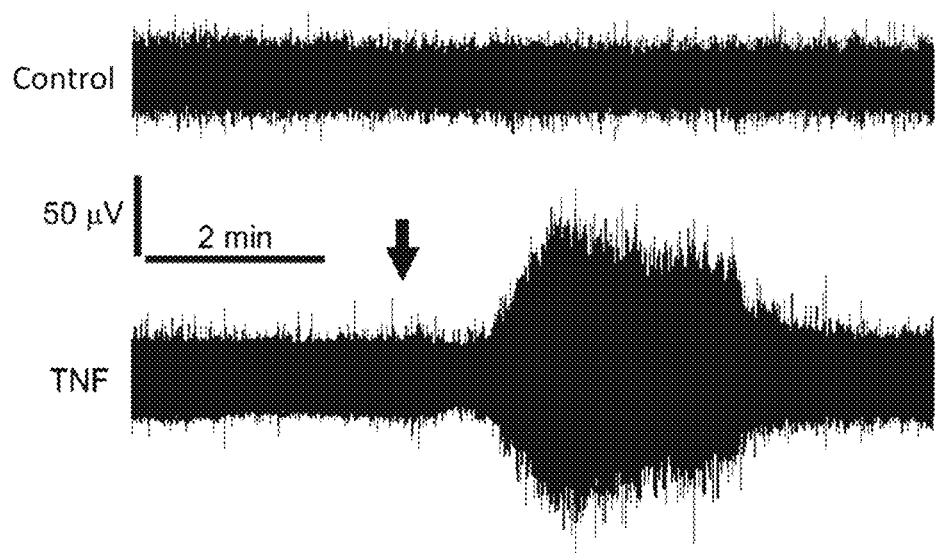
FIG. 2A-2F. Afferent fibers of the vagus nerve carry TNF-induced neurograms. (A) Top, trace showing the spontaneous activity of the cervical vagus nerve. Bottom, trace showing the activity of the cervical vagus nerve after peripheral injection of TNF (dose of 50 μg, marked by arrow). (B) Graph depicting the frequency of CAP firing for the control and TNF-induced neurograms (shown in A). The 10-min period immediately after TNF injection is used to calculate the frequency of CAP firing, as well as the equivalent period from the baseline. (C-D) Diagrams of the surgical vagotomies employed to test the direction of flow of the TNF-induced neurogram. (C) A proximal (Prox.) transection, between the electrodes and the brain, isolates the afferent component, while (D) a distal transection isolates the efferent arm. (E) Graph showing the frequency of CAP firing in 60-sec bins (mean±SEM, line±shaded area) starting 10 min prior to TNF injection (dose of 50 μg) at time zero. Data represent N=3 for each of proximal (filled circles) and distal (open circles) vagotomies. (F) Plot showing CAP frequencies (mean±SEM) for the 10-min periods before and right after TNF in individual mice. The distal transection completely abolishes the TNF effect, which is not affected by the proximal transection (P=0.03 for post values, t test), indicating that afferent fibers are required.
Figure 2B:
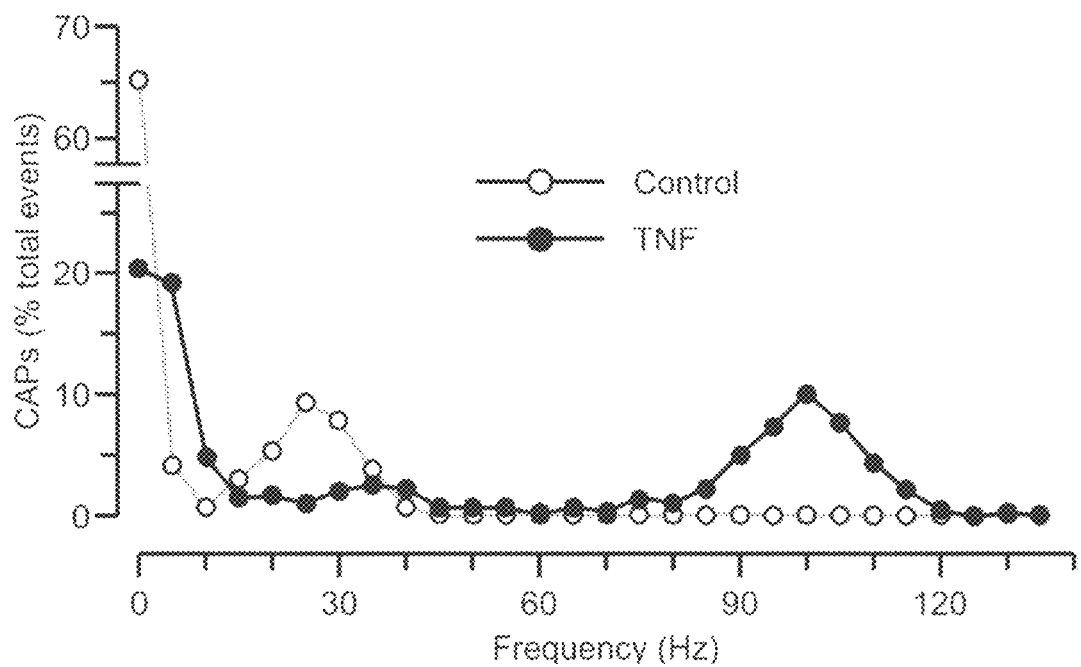
Figure 2C:
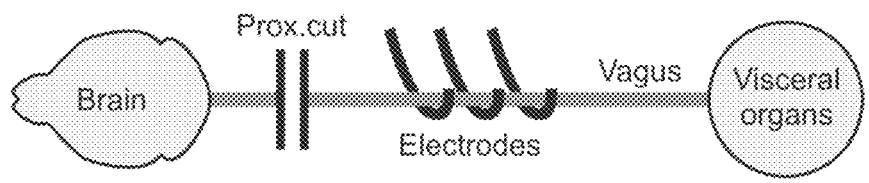
Figure 2D:
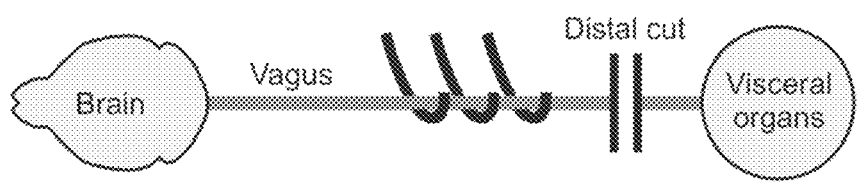

A surgical transection of the vagus nerve was completed either proximal or distal to the hook electrodes, considering the brain as the point of reference (FIG. 2C D). Following placement of the vagus nerve on the hook electrodes, a silk suture was passed under and secured to the vagus nerve with a single knot. Ethyl cyanoacrylate was used to adhere the vagus nerve to the silk suture and the surgical transection completed.

VN Evoked Responses.

The vagus nerve was placed on a wet tissue paper laid over a custom acrylic platform and kept moist using artificial cerebral spinal fluid (126 mM NaCl, 26 mM NaHCO3, 10 mM glucose, 2.5 mM KCl, 2.4 mM $CaCl_2$, 1.3 mM $MgCl_2$, and 1.2 mM $NaH_2PO_4$). A recording electrode (glass pipette filled with 2M NaCl) and a stimulating electrode (FHC, Bowdoin, Me.) were placed onto the vagus nerve, with the latter 4-5 mm away from the former (and farther from the head). Signals were amplified (×1000, model 1800, AM Systems, Everett Wash.) and digitized (30 kHz) through an acquisition system (Micro1400 unit and Spike2 version 7 software, CED, Cambridge, UK). Stimuli (20-μs long) of increasing intensity (1-50 V) were delivered with a stimulator (SD9, Grass, Warwick R. I.) to generate an input/output curves (1-V increments in the 1-10 range, 5-V increments in the 10-50 range), which were generated first in a saline solution and then in the setting of either lidocaine (2%) or tetrodotoxin (100 μM). The responses were assessed by integrating the area between the response curve and the baseline value (determined 1-10 ms prior to stimulation).

Data Analysis.

Spike2 software (version 7, CED) was used for analysis of raw recordings, which were filtered (using high pass filter with an edge of 160 Hz) and smoothed. Neural signals were identified by user-specified adaptive threshold methodology. Identified compound action potentials (CAPs) were reviewed and signals erroneously captured by the adaptive threshold were manually removed. Also ignored were all areas of signal saturation, as well as signals corresponding to cardiac and respiratory components. Following this signal processing, information regarding rate and temporal coding patterns were extracted and further analyzed using Origin-Pro software (version 8, OriginLab, Northampton, Mass.). Neurograms were defined as the first interval of time in which the CAP frequency was >3× baseline level. TNF and IL-1β neurograms were extracted and subjected to Fast Fourier Transform (FFT) for PSD analysis (frequency resolution of 3.9 Hz, using a Hanning window). Within the frequency domain, notch filters were applied (60±10 and 120±10 Hz) to minimize the contribution of electrical noise along with its dominant harmonic. Data were linearly interpolated between the notch-filtered intervals. The areas under the PSDs (20-400 Hz range) were calculated for each cytokine response.

Statistical Tests.

Data are presented as individual samples, mean±SD, and mean±SEM. The Shapiro-Wilk test was used to test for normality. ANOVA, Student t test, Mann-Whitney U test, and Kolmogorov-Smirnov test were used to examine for statistical significance. P values <0.05 were considered significant.

Results

VN Recordings Capture Neural Compound Action Potentials.

Figure 1B:
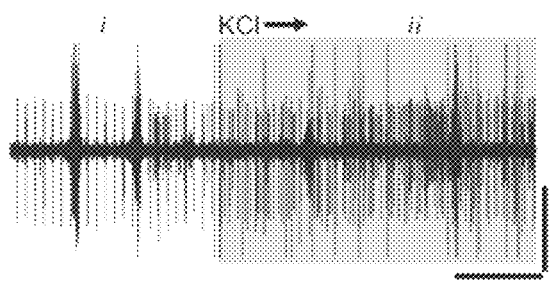
Figure 1C:
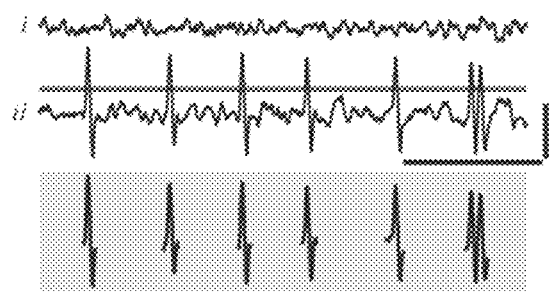
Figure 1D:
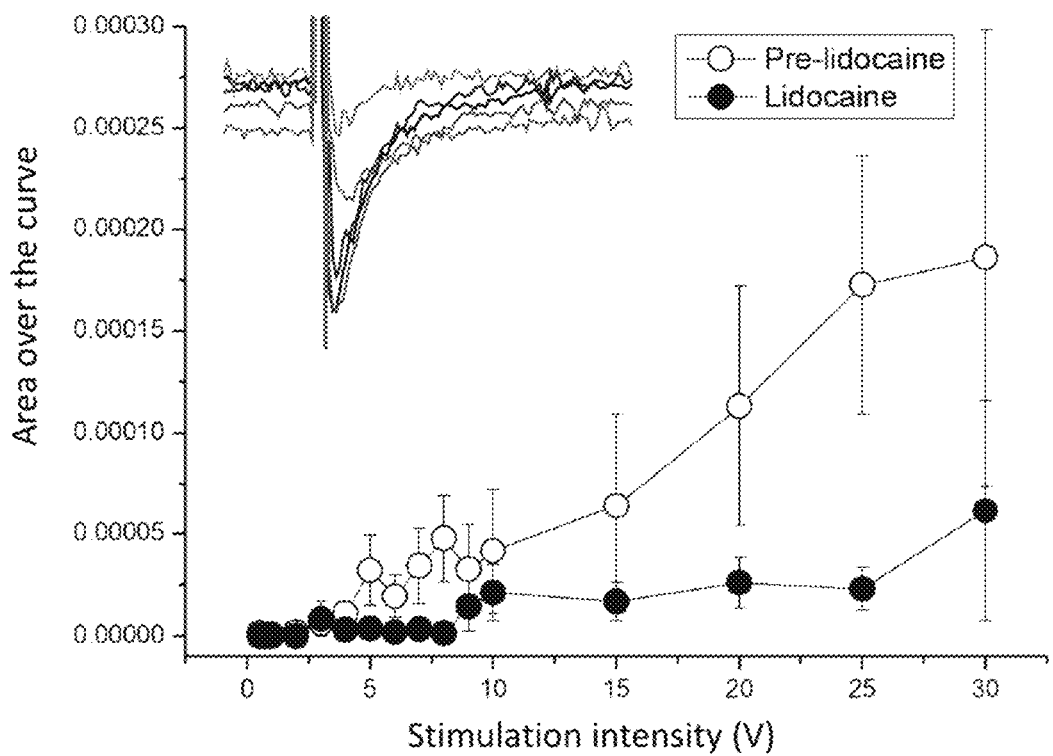
Figure 1E:
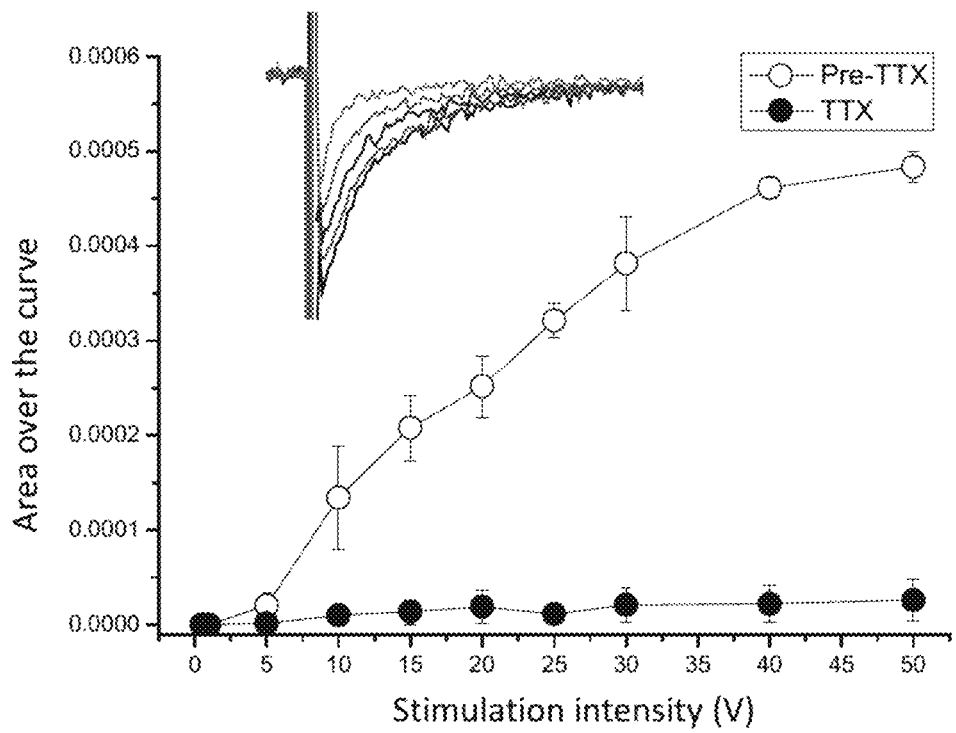

To investigate the vagus nerve's neural activity, an electrophysiological recording system was constructed with three hook electrodes. The signals were digitized, subjected to high-pass filtering, and post-acquisition smoothing algorithms (as described in Methods). The recorded signal showed periodic excursions from baseline that corresponded to the cardiac (amplitude, 30-80 μV, lasting 4-5 ms) and respiratory components (amplitude, ~50 μV, lasting ~120 ms). Notably, contained within the signal, there were discrete, aperiodic spikes of variable amplitude that lasted ~2 ms (FIG. 1A). An adaptive threshold technique was used to identify these fast spikes (FIG. 1B, C) and surmise that they corresponded to compound action potentials (CAPs), which were generated by the near unison firing of multiple axons. To test whether the spikes indeed reflected neuronal activity, nerve activation and inhibition studies were performed. In the former, following baseline acquisition, KCl (4 mM) was applied to the surgical field in close proximity to the vagus nerve so as to depolarize the neural tissue. This treatment produced a significant increase in neural activity (FIG. 1B, C), with individual CAPs showing large amplitude and stereotypical shape (FIG. 1C). By electrically stimulating the vagus nerve preparation with brief pulses of increasing intensities, evoked CAPs of increasing amplitudes were obtained (FIG. 1D, E). Application of lidocaine, a potent anesthetic that blocks sodium channels, resulted in an almost total disappearance of the evoked CAPs (FIG. 1D). Moreover, application of tetrodotoxin, a highly specific sodium channel blocker, abrogated the evoked CAPs completely (FIG. 1E), corroborating the neural nature of the recordings. Remarkably, inhibition of neural activity did not completely eliminate the cardiac and respiratory components, which were likely a composite of electrocardiac signals, electromyographic signals, and motion artifacts (data not shown).

Afferent Nature of the VN Neurograms.

Figure 2E:
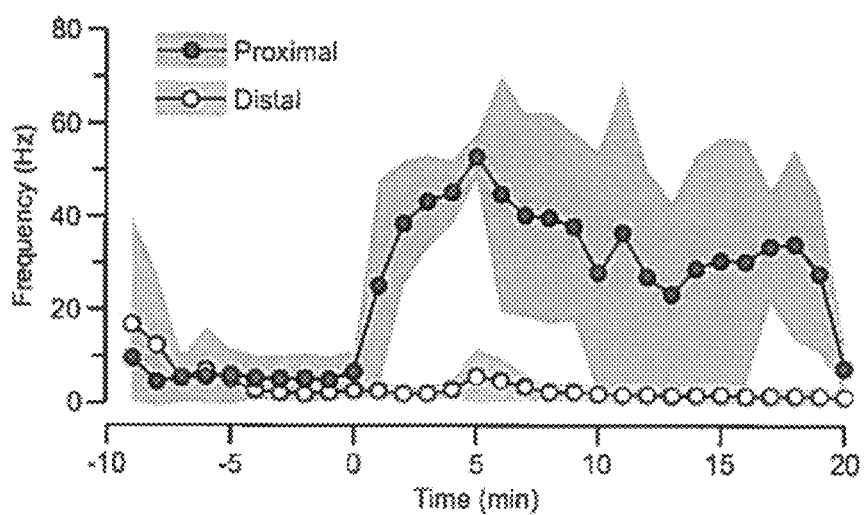
Figure 2F:
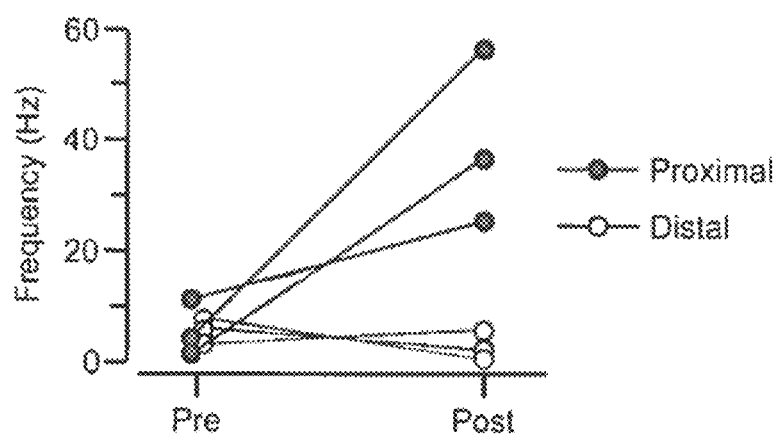

Examination of baseline vagus nerve activity indicated that anesthetized, unstimulated mice showed minimal activation (FIG. 2A) with an underlying mean CAP frequency of 7.6±1.6 Hz (mean±SEM, N=36 recordings lasting >10 min). Traces were divided into 60-sec intervals, which revealed long periods of complete quiescence (N=85 events with CAP frequency=0) that were punctuated by brief periods of strong neural activity. The CAP frequency distribution for non-silent events was not normally distributed (N=275, P=0, W=0.69, Shapiro-Wilk test), with most events occurring at very low frequency and a few occurring at the high-frequency tail (FIG. 2B). An initial test of the hypothesis that an organism's peripheral inflammatory status may represent a component of the vagus nerve's sensory function was performed by applying TNF (50 μg in 200 μL, i.p.), while continuously recording vagus nerve activity. The resulting post-injection neurogram showed an acute increase in neural activity (FIG. 2A), with a fraction of CAPs occurring at much higher frequency than baseline (FIG. 2B). The enhanced neurogram following TNF administration might reflect sensory signals, motor signals, or even both, traveling through the vagus nerve. To directly test the signal directionality, proximal and distal vagotomies (relative to the brain) were performed prior to administering TNF (FIG. 2C, D). With a proximal transection, the afferent fibers tracking towards the recording electrodes from the visceral organs remained intact while efferent fibers no longer interface with the electrodes. The opposite was true with the distal vagotomy, in which the recording electrodes no longer accessed afferent fibers but the efferent fibers remained intact. For each experiment, CAPs were identified and the mean CAP frequencies were plotted across recordings (FIG. 2E). To evaluate the responses, 10-min intervals immediately before and after TNF injection were considered. With proximal vagotomy, the CAP frequency showed a significant increase from baseline (pre, 5.8±2.8, post, 39.5±9.1 Hz, mean±SEM). In stark contrast, distal vagotomy resulted in a null enhancement (pre, 5.7±1.3, post, 2.9±1.5 Hz, mean±SEM). Comparison of the individual post-injection CAP frequencies (FIG. 2F) further demonstrated the significant difference between proximal and distal transections (P=0.03, T=3.28, t test). These data indicate that the first response recorded in the cervical vagus nerve neurograms, following cytokine administration, includes and requires the vagus nerve's sensory function.

VN Neurograms Induced by Pro-Inflammatory Cytokines.

Figure 3A:
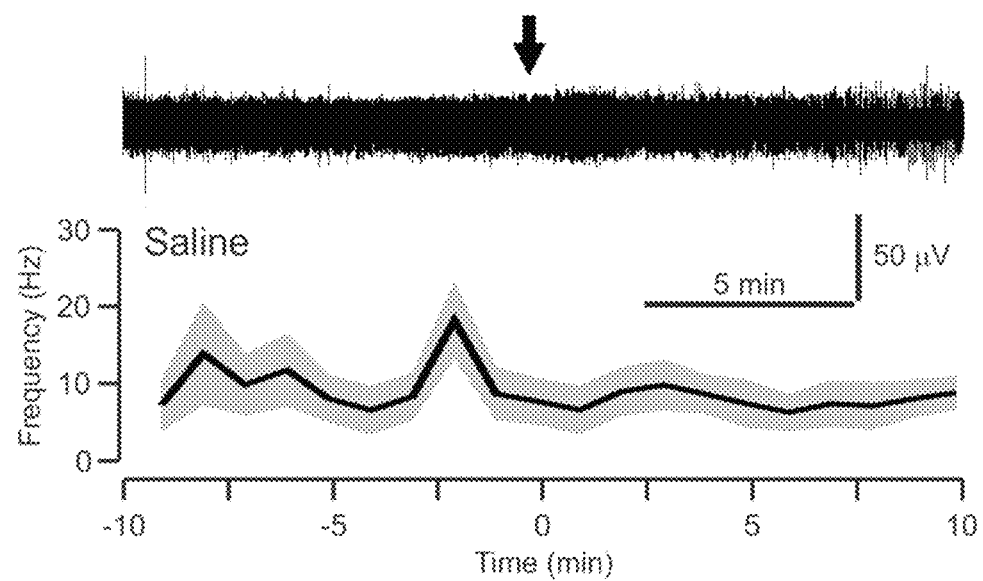
FIG. 3A-3E. Time course for TNF and IL-1β mediated neurograms. (A) Top, trace showing the vagus nerve activity under vehicle (200 μL of sterile saline, marked by arrow), which is used as control. Bottom, graph describing the frequency of CAP firing (mean±SEM, grey area) for N=5 mice, starting 10 min prior to saline injection. (B) Top, representative neurogram for TNF (dose of 50 μg, marked by arrow). Bottom, graph showing the mean frequency±SEM (blue area) for N=6 mice. (C) Top, representative neurogram for IL-1β (dose of 350 ng, marked by arrow). Bottom, graph showing the mean frequency±SEM (green area) for N=8 mice. (D) Plot depicting the frequency of CAP firing (mean±SEM) for TNF at low dose (5 μg, N=6) and high dose (50 μg, N=6). 'Pre' refers to the 30-sec interval just before injection, and 'Post' to the 30-sec interval 5 min post-injection. (E) Plot depicting the frequency of CAP firing (mean±SEM) for IL-1β at low dose (35 ng, N=8) and high dose (350 ng, N=8). 'Pre' refers to the 30-sec period just before injection, and 'Post' to the 30-sec period 2.5 min post-injection.
Figure 3B:
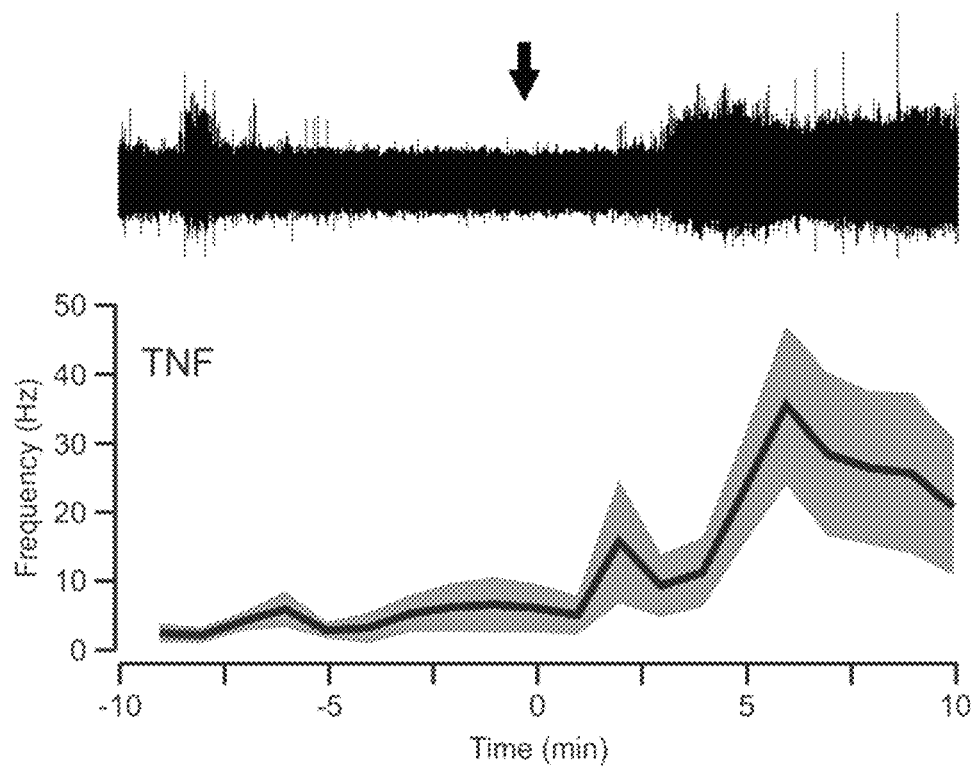

To further dissect the neural activity associated with inflammatory stimuli, the patterns of responses between TNF and IL-1β were compared using exogenous, purified pro-inflammatory cytokines that were injected into the peritoneal cavity. Saline injection was used as the control (FIG. 3A). Application of TNF (50 μg in 200 μL, i.p.) was followed by a notable increase in activity (FIG. 3B). Analysis of 10-min intervals (immediately before and after TNF) revealed a significantly higher mean CAP frequency after TNF (pre, 4.1±3.7, post, 19.8±4.2 Hz, N=6, P=0.013, U=2, Mann-Whitney [MW] test). The peak CAP frequency, defined as the maximum value within the interval, was also significantly elevated after TNF (pre, 19.8±5.9, post, 69.0±17.8 Hz, N=6, P=0.005, U=0, MW test). Both the initiation and termination of the activity envelopes were rapid, occurring on the order of seconds. Moreover, the period that followed the TNF-induced enhancement had a mean CAP frequency (7.4±4.7 Hz) that was similar to baseline activity.

Figure 3C:
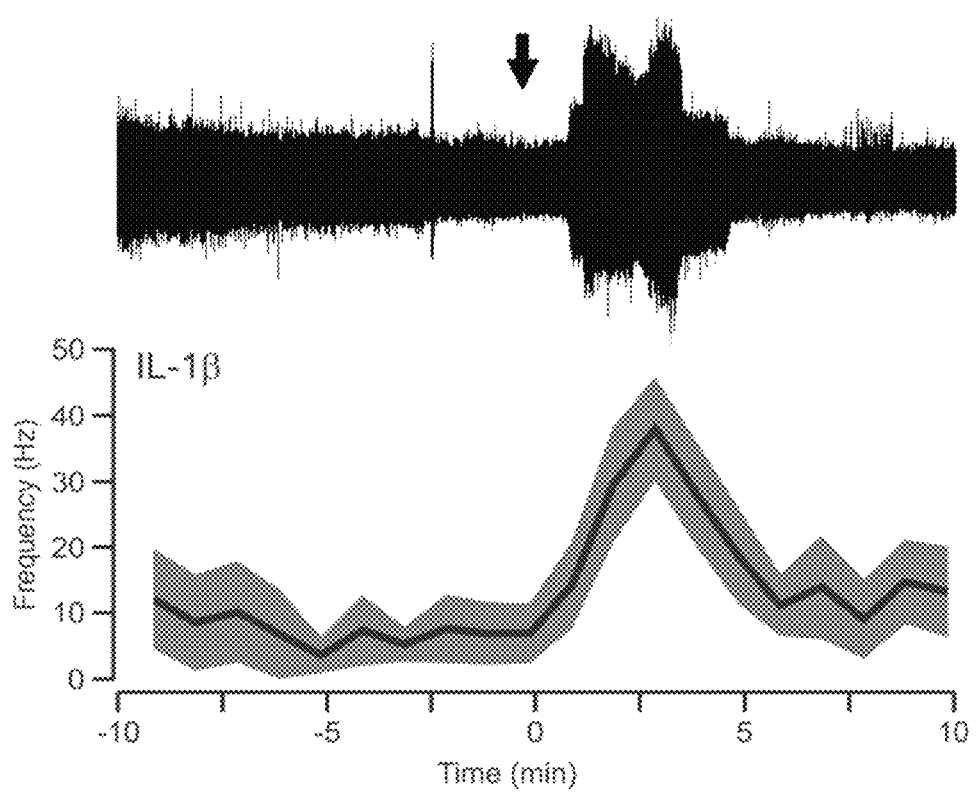

Next, the vagus nerve neurograms were evaluated in the context of injection of IL-1β (350 ng in 200 μL, i.p.). Interestingly, the peak response to IL-1β occurred earlier than that of TNF (FIG. 3C). For this reason, a 5-min interval was used to evaluate the responses immediately before and after injection of IL-1β. The mean CAP frequency was significantly higher following the cytokine (pre, 6.9±3.6, post, 25.5±4.9 Hz, mean±SEM, N=8, P=0.007, U=6, MW test), as well as the peak CAP frequency (pre, 23.9±11.3, post, 74±10.2 Hz, N=8, P=0.013, U=8, MW test). Following the enhanced IL-1β neurogram, the mean CAP frequency returned to baseline level (4.4±1.9 Hz). Importantly, the increased vagus nerve activity that was triggered by cytokines did not reflect physical trauma or disruption to the peritoneal cavity and its viscera because i.p. injection of vehicle alone (200 μL of sterile saline) did not elicit a change in vagus nerve activity (FIG. 3A), as evidenced by the mean CAP frequency (pre, 11.9±4.9, post, 9.6±4.1 Hz, N=5, P=1, U=12, MW test) and the peak frequency (pre, 106.6±23.0, post, 46.0±11.1 Hz, N=5, P=0.037, U=23, MW test).

Figure 3D:
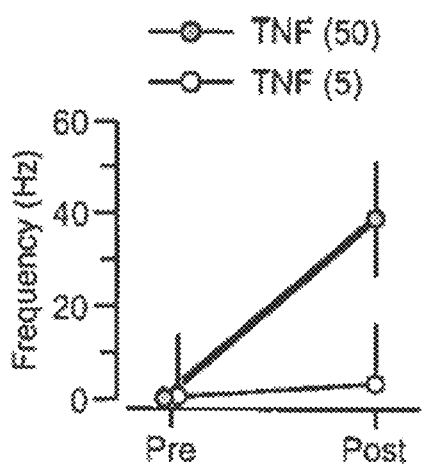
Figure 3E:
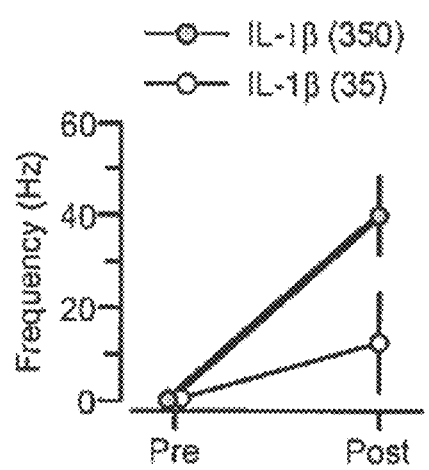

To investigate the dose dependency of the cytokine-induced neurogram enhancement, the amount of administered pro-inflammatory cytokine was titrated. Decreasing the TNF amount ten-fold (5 μg in 200 μL, i.p.) largely abolished the peak response observed 5 min after injecting the higher dose (50 μg) of TNF (FIG. 3D). Similarly, the CAP frequency did not increase in 150 sec following IL-1β administration when it was decreased ten-fold (35 ng in 200 μL, i.p.) (FIG. 3E). The shorter time intervals used for IL-1β compared with TNF reflected the different temporal profiles of neurogram activation to IL-1β compared with TNF. In particular, the IL-1β response peaked earlier (150 sec post-injection) as compared with TNF (300 sec post-injection).

Differences Between Neurograms Induced by TNF and IL-1β.

Comparison of the mean CAP frequencies (FIG. 4A), pre- and post-treatment, revealed significant differences between the saline, TNF and IL-1β groups (P=0.0125, F [2, 21]=5.57, one-way ANOVA). Post-hoc tests also showed that the TNF and IL-1β values were each significantly different to saline (TNF, P=0.006, U=2; IL-1β, P=0.01, U=7, MW test). However, there was no difference between the pro-inflammatory cytokines (P=0.65, U=20, MW test). Analysis of the peak CAP frequency (FIG. 4B), pre- and post-treatment, showed a statistical significance between the three groups (P=6.5× 10-4, F [2, 21]=11.07, ANOVA). Post-hoc tests also demonstrated that the TNF and IL-1β peak responses were each significantly different from saline (TNF, P=0.002, U=0; IL-1β, P=0.003, U=3, MW test). Additionally, the peak CAP frequency changes between pro-inflammatory cytokines were not significantly different (P=0.95, U=23, MW test). The temporal profiles of neurogram activation with TNF and IL-1β treatments were compared by defining the beginning of the response as the time at which the CAP frequency increased to 3× the pre-injection rate, and the response termination as the time when the frequency decreased below the same value. Using these definitions, the latency, duration, and mean CAP frequency for the responses were analyzed (FIG. 4C). The neurograms induced by TNF (N=6) and IL-1β (N=7) had different latencies (TNF, 156.2±40.4, IL-1β, 47.6±15.2 sec, P=0.043, T=2.52, t test). In contrast, the response duration (TNF, 185.2±47.2, IL-1β, 222.6±73.8 sec, P=0.68, T=0.43, t test) and mean CAP frequency (TNF, 35.92±5.2, IL-10, 42.7±4.6 Hz, P=0.35, T=0.97, t test) were not different.

Receptor Requirement for the Neurograms Induced by TNF and IL-1β.

Figures 5A, 5B:
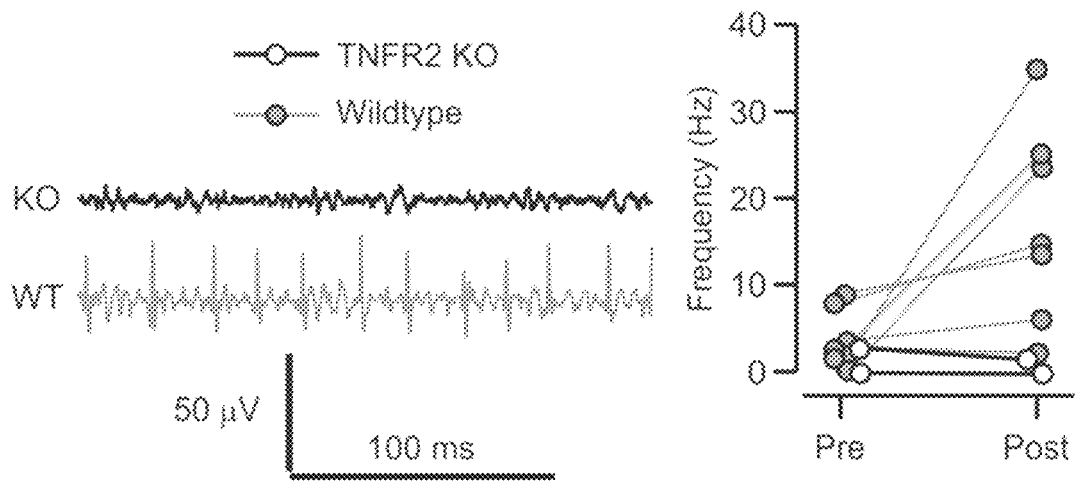
FIG. 5A-5D. Ablation of cytokine-mediated neurograms in TNFR2 and IL-1R deficient mice. (A) Representative traces 5 min after the application of TNF (dose of 50 μg) in TNFR2 KO and WT mice. (B) Plot showing individual CAP frequencies immediately prior and after TNF (10-min intervals) in TNFR2 KO (N=3) and WT animals (N=6) (C) Representative traces 150 sec after the application of IL-1β (dose of 350 ng) in IL-1R KO and WT mice. (D) Plot showing individual CAP frequencies immediately prior and after IL-1β (5-min intervals) in IL-1R KO (N=3) and WT animals (N=8).
Figures 5C, 5D:
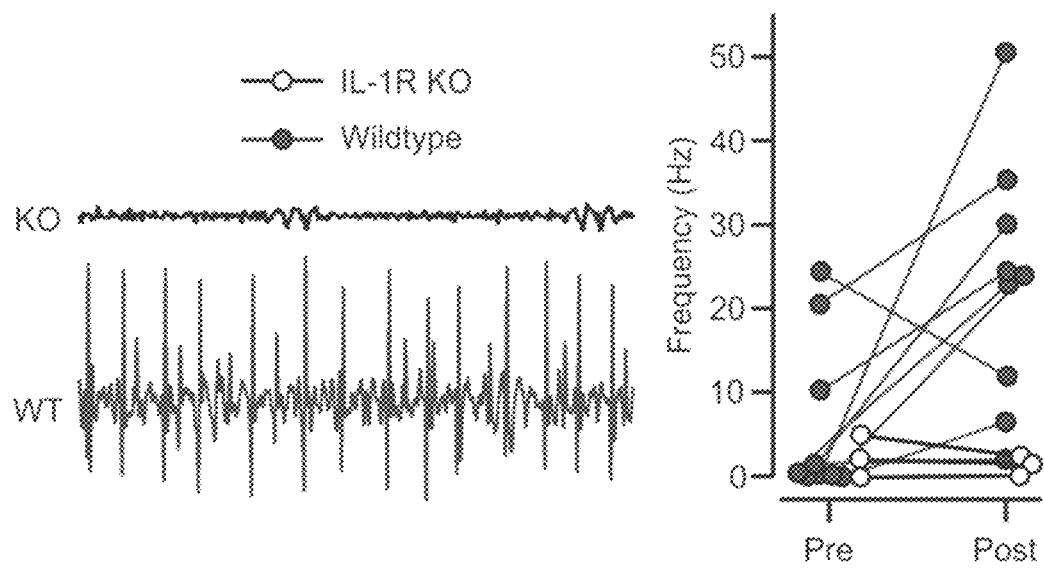

It has previously been demonstrated that TNF trimers can form receptor-independent transmembrane channels (19). In this case, the administration of TNF could in theory directly activate neurons without engaging its receptor. To test whether the cytokine-induced responses required cytokine-receptor signaling, the vagus nerve neurograms from receptor knockout (KO) mice were recorded. TNF injection in TNFR2 KO mice did not lead to a change in the neurogram (FIG. 5A, B), implicating a ligand-receptor interaction in the observed response enhancement. Next, the requirement for the IL-1β receptor (IL-1R) in the IL-1β-induced neurogram activation was tested. Exogenous IL-1β did not stimulate the cervical vagus nerve in IL-1R KO mice (FIG. 5C, D). In all KO mouse experiments in which no clear response was observed, KCl (4 mM) was applied to the nerve at the termination of the experiments to ensure vagus nerve viability (data not shown). Additionally, in complementary cross-over studies, i.p. administration of IL-1 in TNFR1/R2 double KO mice did induce an increase in vagus nerve signaling (data not shown). Similarly, IL-1R KO mice responded to i.p. administration of TNF with increased vagus nerve activity (data not shown).

To test the requirement of full length TNF for vagal nerve activation, recombinant human TNF was digested in 0.05% trypsin overnight at 37 deg C. The trypsin was heat-inactivated by incubating the solution at 95 deg C. for 7 min. A digestion of approximately 90% was confirmed by SDS-PAGE gel. Digested or full-length TNF (50 g/animal) was injected into the peritoneum while continuously recording from the cervical vagus nerve. As expected, trypsin-digested TNF did not reproduce the effects of full-length TNF on vagal nerve activation (data not shown).

Spectral Power of the VN Signals Induced by TNF and IL-1β.

Figures 6A, 6B:
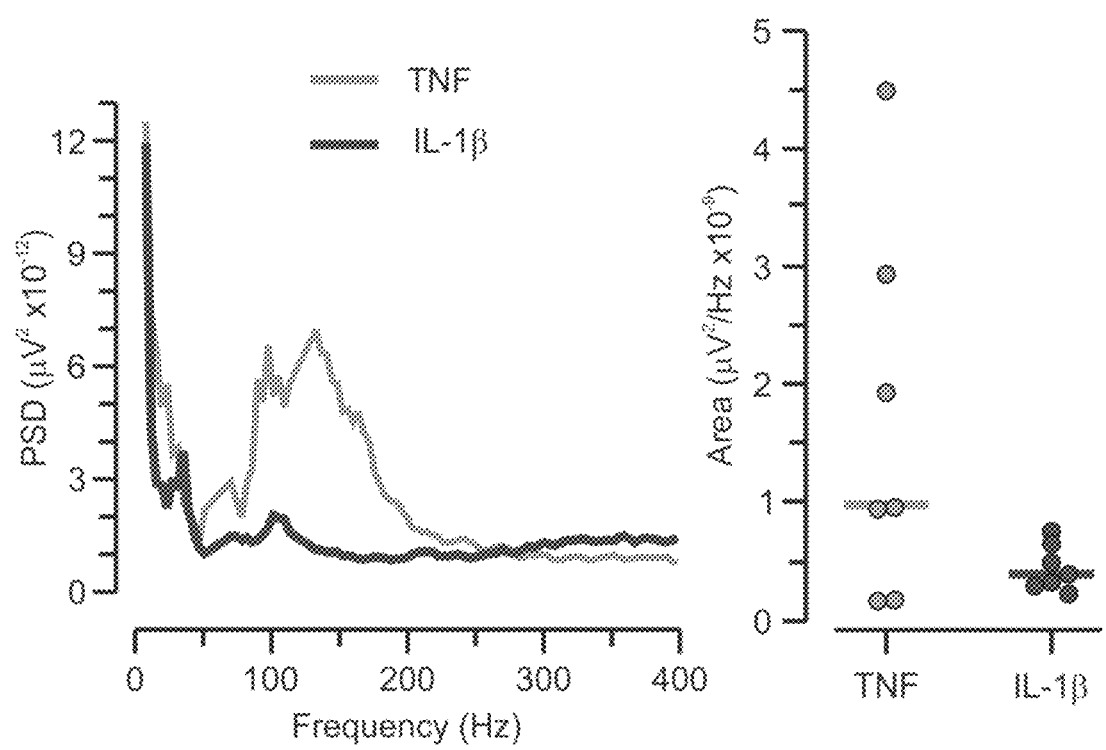
FIG. 6A-6B. Spectral analysis of TNF and IL-1β mediated neurograms. (A) Representative power spectral densities (PSD) for the TNF and IL-1β responses in the unfiltered neurogram recordings. (B) The areas under the PSDs (20-400 Hz range) were calculated for TNF and IL-1β. The calculated area for each response is shown for TNF and IL-1β, along with group averages (lines). Responses are statistically different (N=7 for each group; P=0.05, D=0.71, Kolmogorov-Smirnov test), suggesting a potential biological substrate for cytokine discrimination within the CNS.

Given that TNF and IL-1β elicit similar, but not identical, enhancements in the vagus nerve neurograms and that these cytokine receptor-dependent signals involved afferent fibers, it was examined whether the vagus nerve is capable of sending distinct signals about TNF and IL-1β to the CNS. To investigate this possibility, the power spectral densities (PSDs) of the TNF and IL-1β responses were analyzed, using unfiltered neurogram recordings. As above, the response was defined as the first interval of time in which the CAP frequency resided at 3× the baseline level. Representative PSDs for TNF and IL-1β are shown in FIG. 6A. Next, each filtered PSD was integrated (from 20 to 400 Hz) to compare the individual areas of the TNF and IL-1β responses (FIG. 6B). Statistical analysis revealed a significant difference between TNF and IL-1β groups (N=7, P=0.05, D=0.71, Kolmogorov-Smirnov test). Together, the difference in the response temporal characteristics and frequency domain power analyses indeed demonstrated a selective cytokine neural sensory signaling through the vagus nerve.

Discussion

The work presented here adds to the rapidly expanding literature describing the interface between neuroscience and immunology, delineating for the first time the afferent arc of the inflammatory reflex. Use of surgical vagotomies verified the postulate that afferent fibers of the vagus nerve can function as cytokine sensors that relay information to the CNS (5-7). Moreover, analysis of neurograms for TNF and IL-1β reveal selective, specific, afferent signaling of the vagus nerve in response to respective pro-inflammatory cytokines.

Receptor knock out (KO) mice were used to study the receptor dependency of the sensory component of the inflammatory reflex. The complete absence of neurogram enhancement in receptor KO animals matched to administered cytokine (but not in receptor KO animals mis-matched to the administered cytokine) implicates the corresponding cytokine receptor in specific cytokine-induced activation of the vagus nerve. In brief, cytokine-receptor interactions mediate the neurogram response. At the cellular level, the mechanism by which systemic cytokines elicit neuronal activation in the vagus nerve remains an active area of research. Several studies have demonstrated the presence of functional cytokine receptors within neuronal populations, such that activation of these receptors is capable of modulating neuronal excitability (10-12). A recent report has shown that bacterial products can directly activate a specific population of sensory neurons (13). It follows that the pro-inflammatory cytokines may directly activate sensory vagus nerve fibers within the peritoneum. Alternatively, intermediate populations of receptor-expressing somatic cells may be required to sense the cytokine and, in turn, stimulate the neurons.

Remarkably, the differences between TNF and IL-1β indicate that the CNS can discriminate between a diverse set of inflammatory mediators. This notion has a strong teleological basis because the CNS receives a continuous sensory flow pertaining to the internal body environment, of which the signals that relay systemic inflammation must constitute a key element for an animal's homeostasis and survival. With the rapid delivery of signals on peripheral inflammatory (and immune) status, an organism would be better able to initiate appropriate physiological and behavioral responses to immunological and environmental challenges.

In addition to the observed temporal differences in neurogram enhancement between TNF and IL-1β, the spectral densities of the individual responses (FIG. 6) provide further evidence for the existence of discriminating features between the cytokine-elicited vagus nerve activities that could be interpreted by CNS centers, such as the nucleus tractus solitarius. There is ample evidence that many cortical and subcortical structures within the CNS can distinguish the spectral characteristics of signals and use them in processes as diverse as memory encoding, decision making, and switching between sleep states (14-16). Either alone or in combination, the observed differences in time and frequency domain metrics may represent the biological substrate for the discrimination of peripheral cytokines by the CNS.

The interface between neuroscience, immunology, and clinical medicine is increasingly moving to the fore, especially as the use of electrical devices as therapeutic agents for disease becomes a reality and shapes the emerging field of bioelectronic medicine (17). For instance, a recent clinical trial that used vagus nerve stimulation to treat rheumatoid arthritis proved successful (18).

Figure 7:
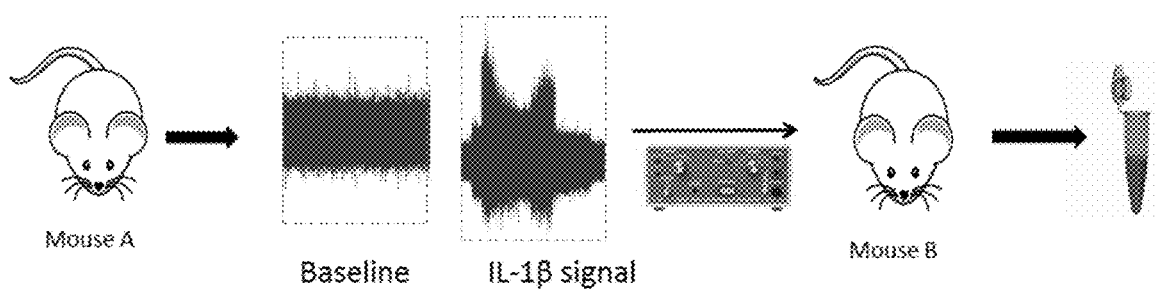
FIG. 7. Paradigm to induce inflammatory phenotype in naïve mice by acoustic stimulation using IL1β-specific signal. A baseline or IL1β-specific signal is extracted from a vagus neurogram obtained from mouse A, and converted to 'wav' file. The baseline or IL1β specific signal was transferred to another naïve receiver mouse B by acoustic stimulation. Circulating cytokine levels were analyzed in mouse B after 1 hr.
Figure 8A:
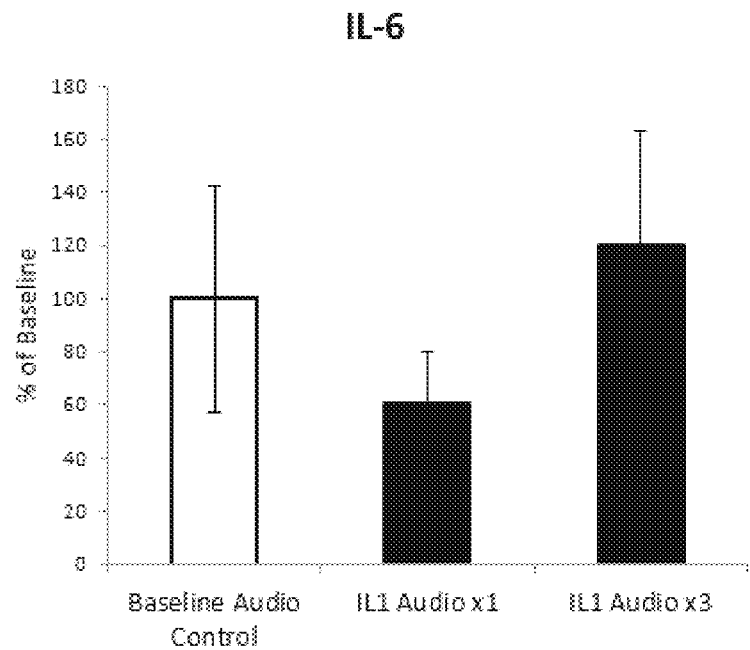
FIG. 8A-8E. Acoustic stimulation using IL1β-mediated neurogram induced increased levels of circulating inflammatory cytokines. Naïve animals receive acoustic stimulation using baseline or IL1β-mediated neurogram signal (1× or 3× serial activation). IL1β-specific but not the baseline signal induced inflammatory phenotype in naïve receiver mice. Levels shown for (A) IL-6; (B) IL1β; (C) TNF-α; (D) IL-10; and (E) IL-8.
Figure 8B:
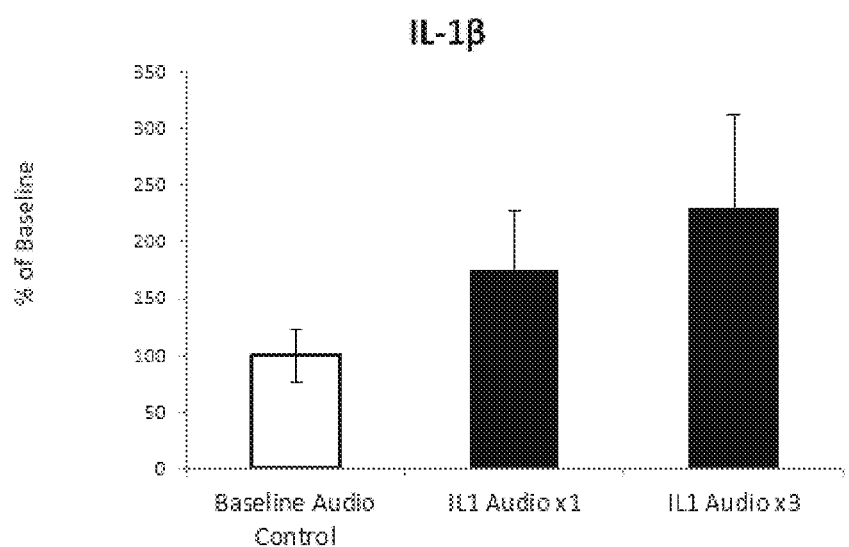
Figure 8C:
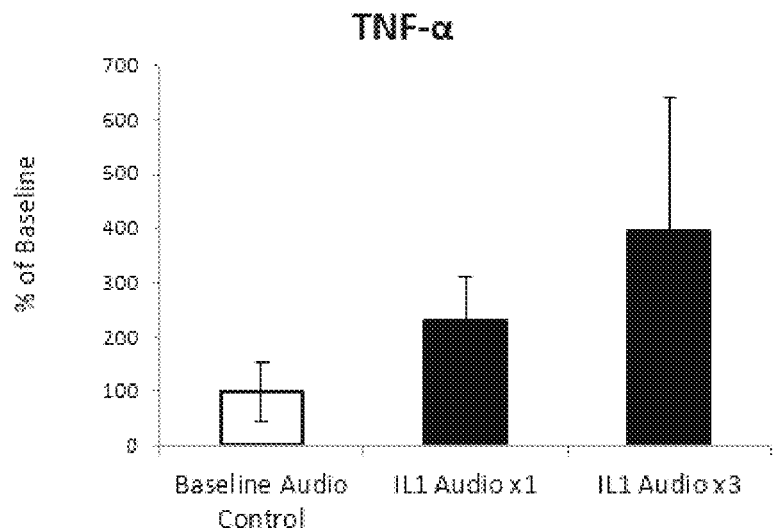
Figure 8D:
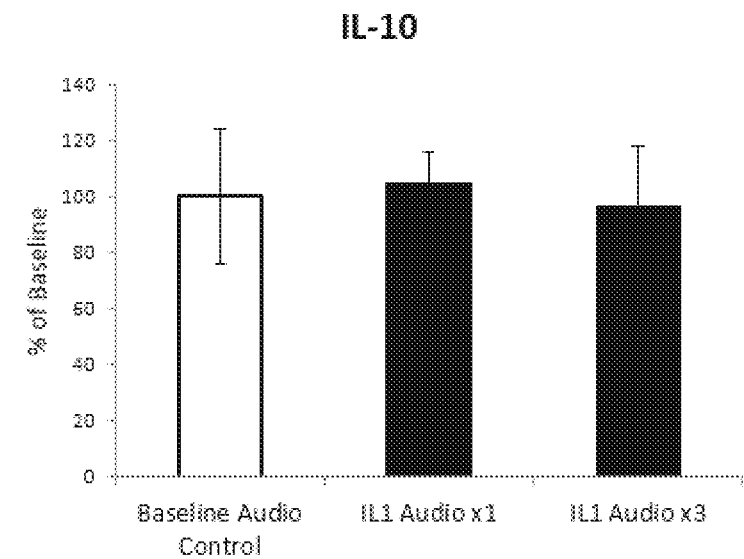
Figure 8E:
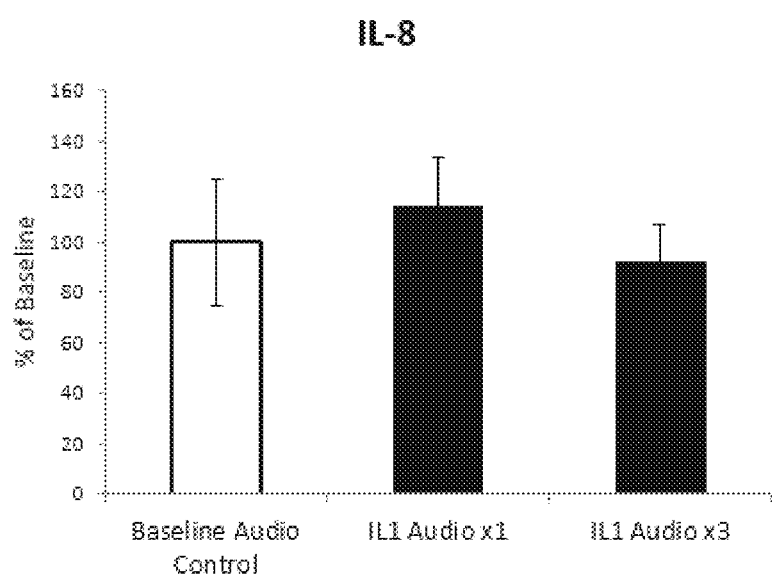

Example 2. Acoustic Stimulation Using IL1β-Mediated Neurogram Induces Increased Levels of Circulating Inflammatory Cytokines The paradigm for inducing an inflammatory phenotype in naïve mice by acoustic stimulation using an IL1β-specific signal is illustrated in FIG. 7. Interleukin-1β(IL-1β)-specific and baseline neurograms were recorded from the cervical vagus nerve of adult mice. Baseline or IL1β-specific signal was extracted from the vagus neurogram obtained from mouse A, and converted to a 'way' file. Baseline or IL1β specific signal was transferred to another naïve receiver mouse B by acoustic stimulation (1× or 3× serial activation). Circulating cytokine levels were analyzed in mouse B after 1 hr. IL1β-specific but not the baseline signal induced an inflammatory phenotype in naïve receiver mice (FIG. 8A-E).

Example 3. Vagus Neurograms Specific for Euglycemia, Hyperglycemia and Hypoglycemia Conditions Recording of Hypoglycemic Neurogram.

Figure 9:
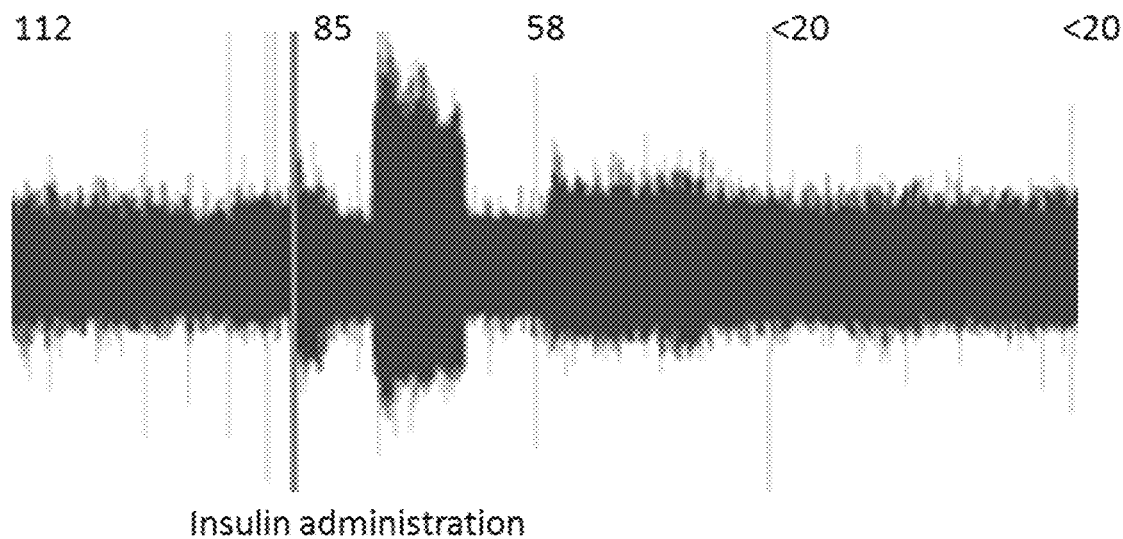
FIG. 9. Recording of hypoglycemic neurogram from the vagus nerve. Naïve mice received a bolus of insulin (6 mg/kg), and vagus nerve activity was recorded over time. The blood glucose levels were monitored every 2.5 min. Insulin induced a hypoglycemic condition in mice, as illustrated by the top line of the figure, which indicates blood glucose levels in mg/dL.

Naïve mice received a bolus of insulin (6 mg/kg), and vagus nerve activity was recorded over time (FIG. 9). The blood glucose levels were monitored after every 2.5 min. Insulin induced a hypoglycemic condition in mice. Blood glucose levels are indicated in the top line of FIG. 11 in mg/dL.

Recording of Euglycemic Neurogram.

Figure 10:
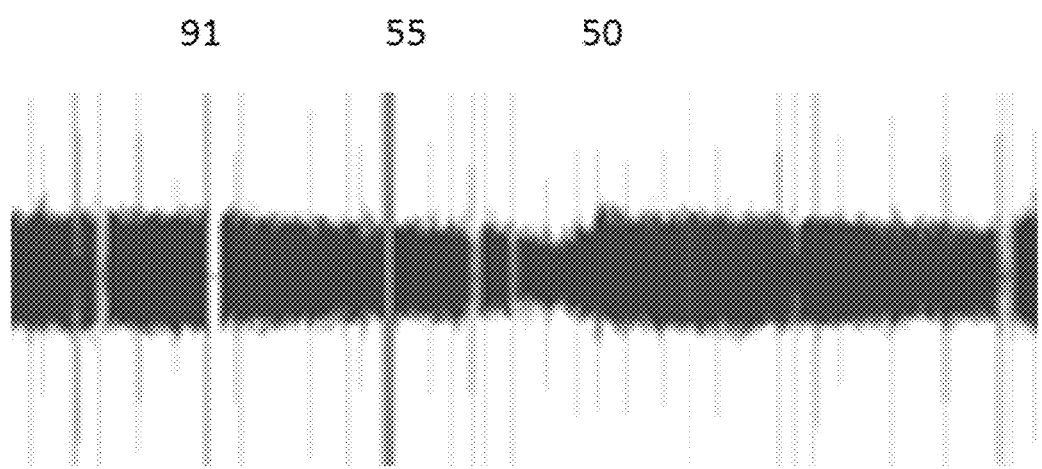
FIG. 10. Recording of euglycemic neurogram from the vagus nerve. Naïve mice received a bolus of glucagon (1 mg/kg), and vagus nerve activity was recorded over time. The blood glucose levels were monitored after every 2.5 min. Blood glucose levels are indicated in the top line of the figure in mg/dL.

Naïve mice received a bolus of glucagon (1 mg/kg), and vagus nerve activity was recorded over time (FIG. 10). The blood glucose levels were monitored after every 2.5 min. Blood glucose levels are indicated in the top line of FIG. 11 in mg/dL.

Figure 11:
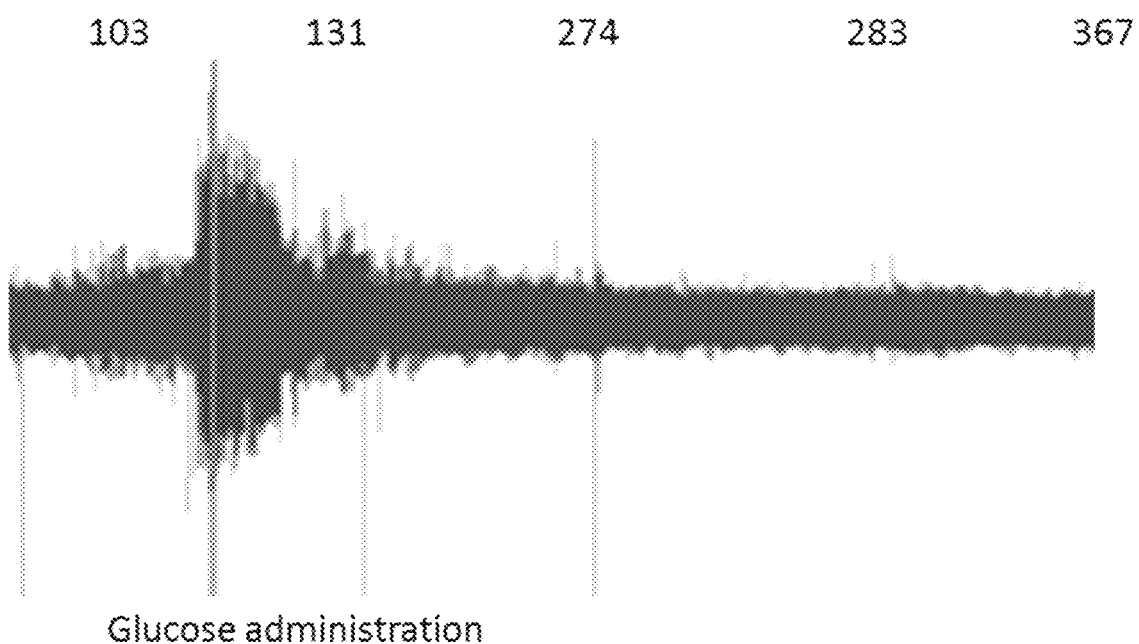
FIG. 11. Recording of hyperglycemic neurogram from the vagus nerve. Naïve mice received a bolus of glucose, and vagus nerve activity was recorded over time. The blood glucose levels were monitored after every 2.5 min. Blood glucose levels are indicated in the top line of the figure in mg/dL.

Recording of hyperglycemic neurogram. Naïve mice received a bolus of glucose, and vagus nerve activity was recorded over time (FIG. 11). The blood glucose levels were monitored after every 2.5 min. Glucose induced a hyperglycemic condition in mice. Blood glucose levels are indicated in the top line of FIG. 13 in mg/dL.

Example 4. Control of Blood Glucose Levels in Human Subjects by Acoustic Playback of Vagal Neurograms Specific for Hyperglycemia or Hypoglycemia Conditions The effects on blood glucose levels in healthy human subjects were determined in response to acoustic playback of hypoglycemia-specific neurograms, hyperglycemia-specific neurograms or euglycemia-specific neurograms.

Figure 12:
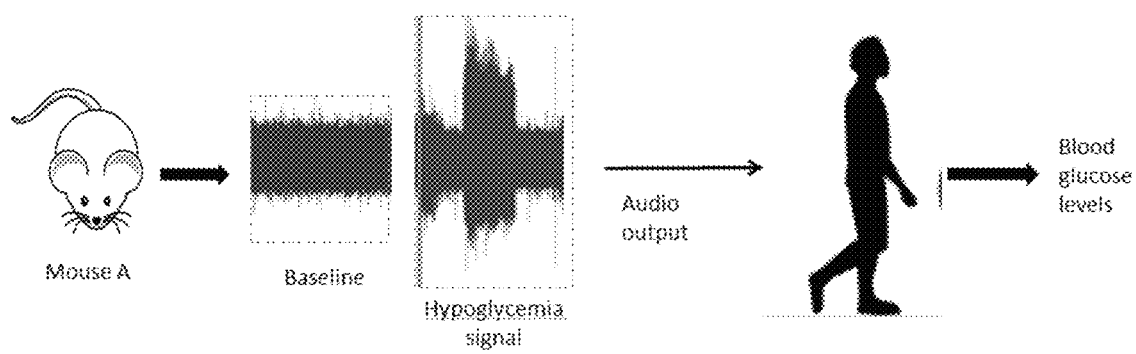
FIG. 12. Paradigm to increase blood glucose levels in healthy human subjects by acoustic stimulation using a hypoglycemia-specific signal. A baseline or hypoglycemia-specific signal was extracted from a vagus nerve neurogram obtained from mouse A. The signal was converted to 'wav' file, and transferred as an audio output to healthy human subjects. Blood glucose levels were monitored in human subjects at regular time intervals.
Figure 13:
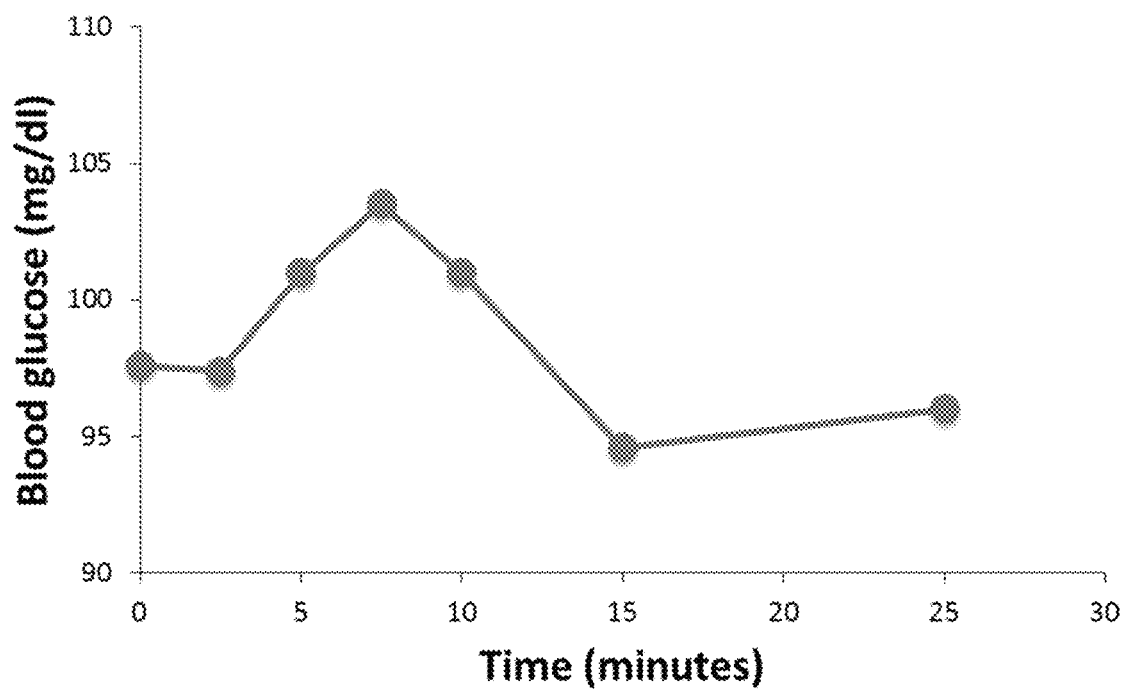
FIG. 13. Acoustic playback of hypoglycemia-specific neurogram induced hyperglycemia in healthy human subjects. Vagus nerve neurograms were recorded from mice receiving a bolus of insulin. The levels of blood glucose decreased in mice receiving insulin. The neurogram was then played as a 'wav' file to healthy human subjects and the blood glucose levels were monitored over time (n=5/group).
Figure 14:
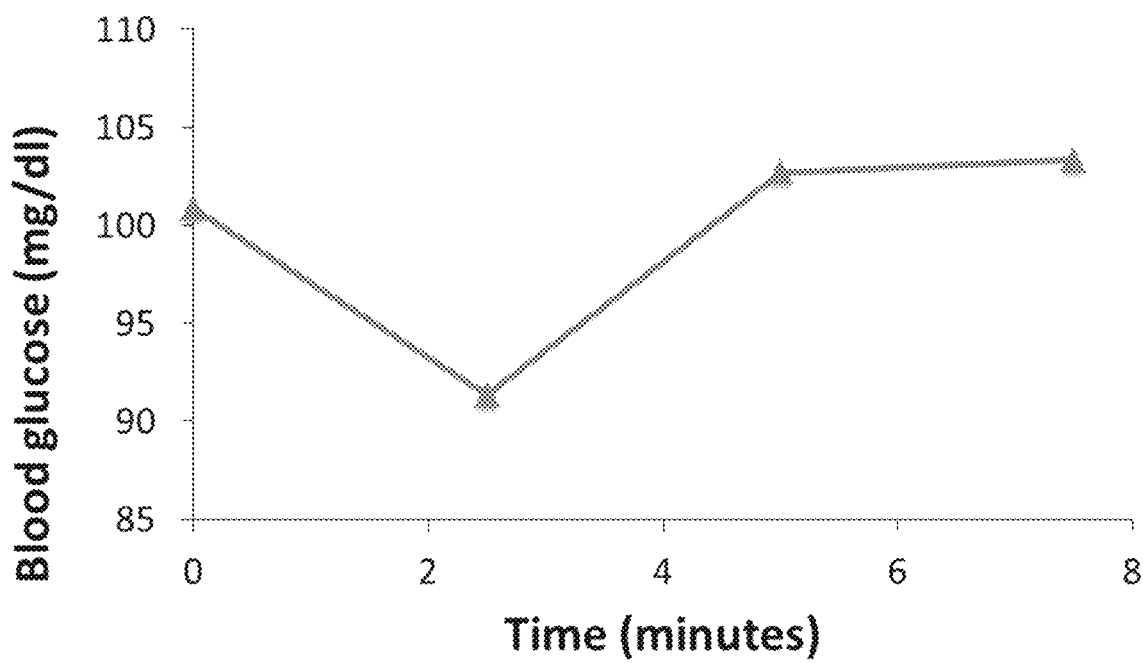
FIG. 14. Acoustic playback of hyperglycemia-specific neurogram induced hypoglycemia in healthy human subjects. Vagus nerve neurograms were recorded from mice receiving a bolus of glucose. The levels of blood glucose increased in the mice receiving glucose. The neurogram was then played as a 'wav' file to healthy human subjects and the blood glucose levels were monitored over time (n=3/group).

FIG. 12 illustrates a paradigm to increase blood glucose levels in healthy human subjects by acoustic stimulation using a hypoglycemia-specific signal recorded from the vagus nerve. Naïve mice received a bolus of insulin (6 mg/kg), and vagus nerve activity was recorded over time. Insulin induced a hypoglycemic condition in mice. The signal was converted to a 'wav' file, and transferred as an audio output to healthy human subjects. Blood glucose levels were monitored in human subjects at regular time intervals. Acoustic playback of the hypoglycemia-specific neurogram induced hyperglycemia in healthy human subjects (FIG. 13).

Figure 15:
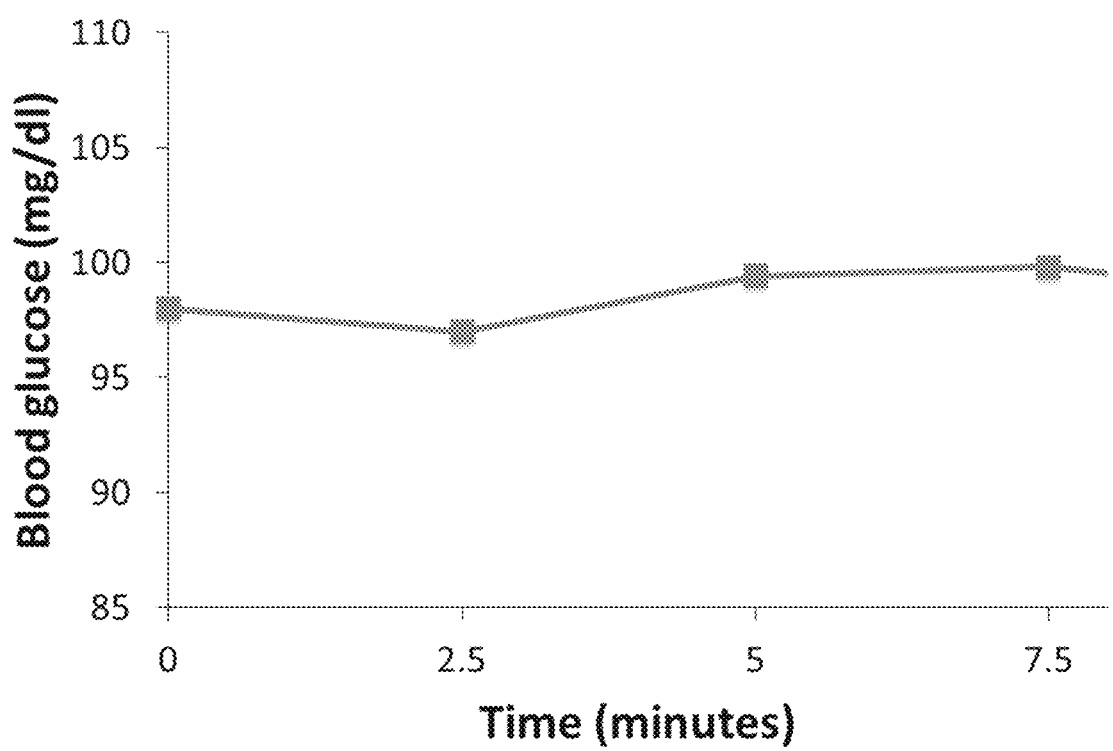
FIG. 15. Acoustic playback of euglycemia-specific neurogram did not induce a change in blood glucose levels in healthy human subjects. Vagus nerve neurograms were recorded from mice receiving a bolus of glucagon. The levels of blood glucose did not change in mice receiving glucagon. The neurogram was then played as a 'wav' file to healthy human subjects and the blood glucose levels were monitored over time (n=5/group).

In another set of experiments, vagus nerve neurograms were recorded from naïve mice receiving a bolus of glucose, and vagus nerve activity was recorded over time. The levels of blood glucose increased in the mice receiving glucose. The vagus neurogram was converted to a 'wav' file, and transferred as an audio output to healthy human subjects. Blood glucose levels were monitored over time (n=3/group). Acoustic playback of the hyperglycemia-specific neurogram induced hypoglycemia in healthy human subjects (FIG. 15).

In a control set of experiments, vagus nerve neurograms were recorded from naïve mice receiving a bolus of glucagon (1 mg/kg), and vagus nerve activity was recorded over time. The levels of blood glucose did not change in mice receiving glucagon. The neurogram was then played as a 'wav' file to healthy human subjects and the blood glucose levels were monitored over time (n=5/group). Acoustic playback of the euglycemia-specific neurogram did not induce a change in the blood glucose levels in healthy human subjects (FIG. 15).

Example 5. Acoustic Playback in Human Subject Using Cortisol-Specific Vagal Neurogram Induces Hyperglycemia Recording of Hydrocortisone Induced Neurogram from Mouse.

Figure 16:
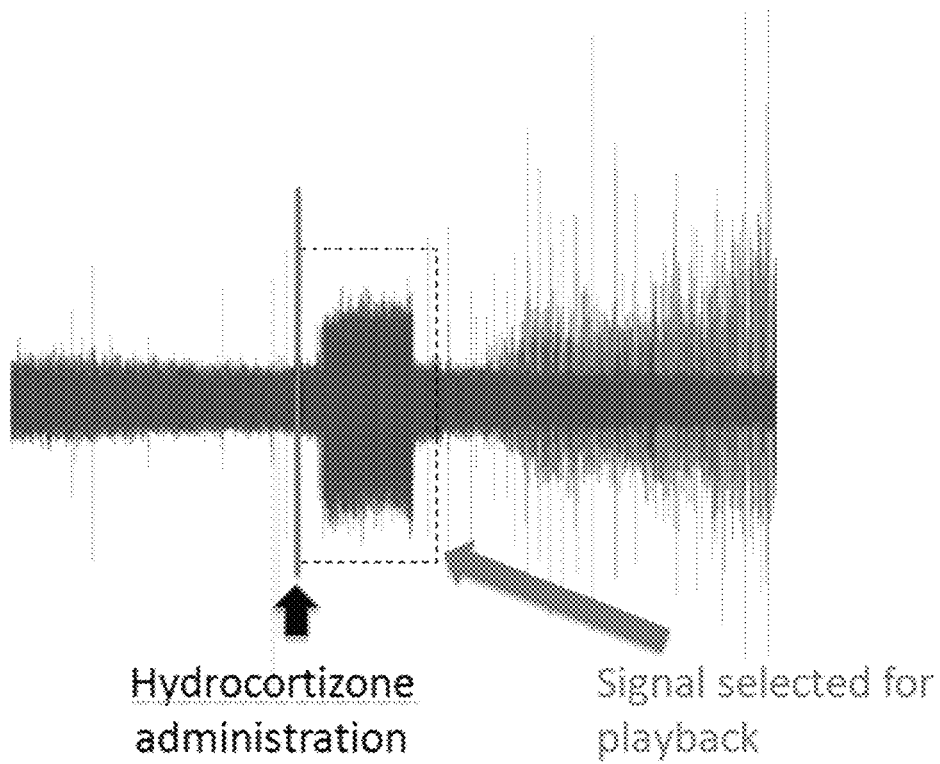
FIG. 16. Recording of hydrocortisone-induced neurogram from a mouse vagus nerve. Naïve mice received a bolus of hydrocortisone (cortisol) (10 mg/mouse), and vagus nerve activity was recorded over time.

Injection of a bolus of hydrocortisone (cortisol) (10 mg/mouse) into naïve mice induced a specific neurogram that was recorded from the vagus nerve (FIG. 16).

Administration of Cortisol Induces Hypoglycemia in Mice.

Figure 17:
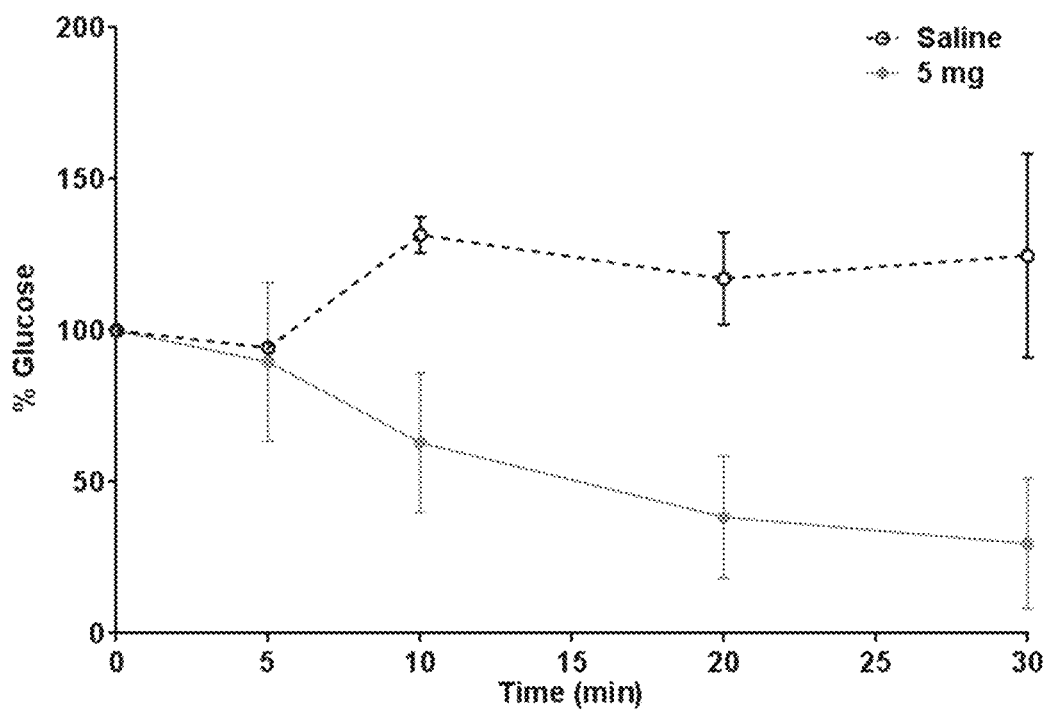
FIG. 17. Administration of cortisol-induced hypoglycemia in mice. Naïve mice received either saline or cortisol by intraperitoneal administration. Blood glucose levels were monitored over time. Cortisol but not saline administration induced hypoglycemia.

Naïve mice received either saline or cortisol by intraperitoneal administration. Blood glucose levels were monitored over time. Administration of cortisol, but not saline administration, induced hypoglycemia (FIG. 17).

Acoustic Playback of Cortisol-Specific Neurogram Induced Hyperglycemia in Healthy Human Subjects.

Figure 18:
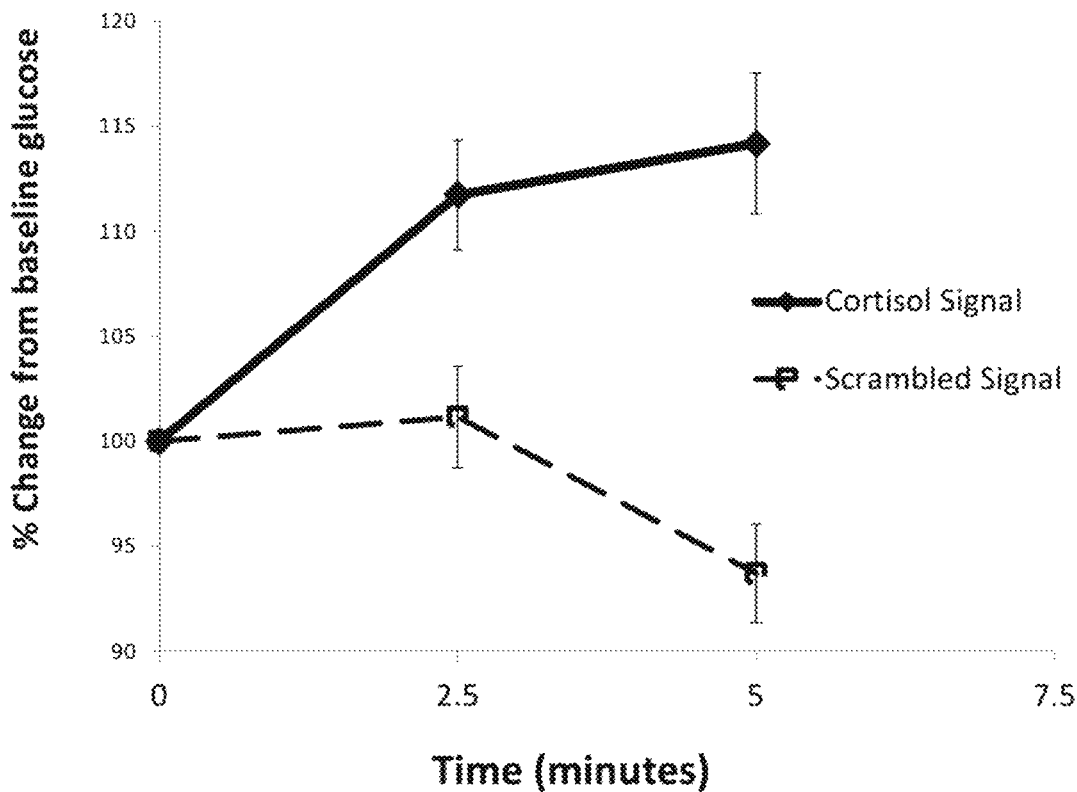
FIG. 18. Acoustic playback of cortisol-specific vagus nerve neurogram induced hyperglycemia in healthy human subjects. Vagus nerve neurograms were recorded from mice receiving a bolus of hydrocortisone. A "scrambled signal control" was generated by transforming the cortisol-specific signal into a scrambled signal using a matlab code that generates a randomized signal with the same amplitudes, but random frequencies, maintaining the total power of the signal. The cortisol-specific neurogram or scrambled signal was then played as a 'wav' file to healthy human subjects and the blood glucose levels were monitored over time. (n=8/group).

A cortisol-specific signal was extracted from a neurogram obtained from the vagus nerve of a mouse following i.p. administration of cortisol. To generate a control signal, the cortisol-specific signal was transformed to a scrambled signal using a matlab code that generates a randomized signal with the same amplitudes, but random frequencies, maintaining the total power of the signal. The cortisol-specific or scrambled signal was converted to a 'wav' file, and transferred as an audio output to healthy human subjects. Blood glucose levels were monitored in human subjects at regular time interval. Acoustic playback of cortisol-specific neurogram induced hyperglycemia in healthy human subjects (FIG. 18).

Figure 19:
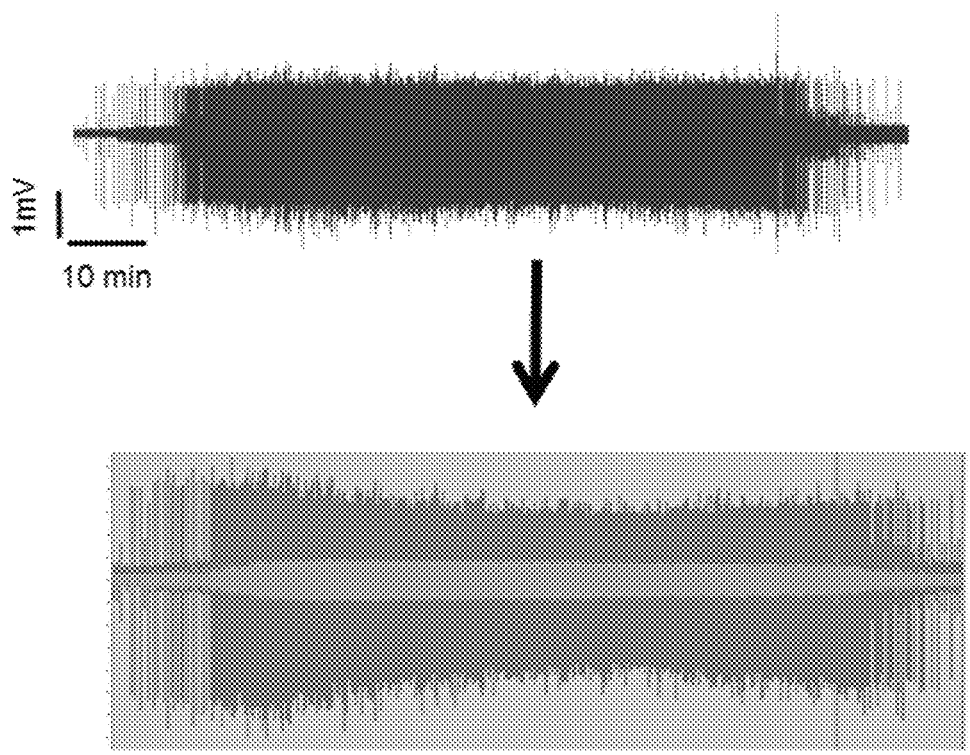
FIG. 19. Dexamethasone-specific neurogram. Upper: A dexamethasone-specific neurogram is extracted from the cervical vagus nerve following intraperitoneal administration of dexamethasone in a mouse. Lower: The neurogram signal is converted to .wav file on a 15 kHz carrier frequency.

Example 6. Treatment of Inflammation Using Acoustic Playback of Dexamethasone-Specific Vagal Neurogram Balb/c male mice were anesthetized with isofluorane, and placed on the surgery table in the supine position. The left cervical branch of the vagus nerve was separated from the surrounding tissue, and placed on a bipolar electrode. A ground electrode was placed under the skin at the cervical level. After a baseline recording, dexamethasone was administered intraperitoneally, and compound action potentials were recorded on the cervical vagus nerve. A dexamethasone-specific signal was extracted from the vagal neurogram and converted to '.wav' file on a 15 kHz carrier frequency (FIG. 19). As a control, a scrambled dexamethasone signal was generated.

Figure 20:
FIG. 20. Suppression of inflammatory responses in endotoxemic mice by acoustic stimulation using a dexamethasone-specific signal. A dexamethasone-specific signal was extracted from a vagal neurogram obtained from mouse A, and converted to a '.wav' file on a 15 kHz frequency. As a control, the signal was scrambled. Control or dexamethasone-specific signal was transferred to a naïve receiver mouse B by acoustic stimulation. Animals were subjected to acoustic stimulation once per day for 6 days. Animals were challenged with endotoxin after 30 min. Circulating TNF levels were analyzed in mouse B 90 min post-endotoxin.
Figure 21:
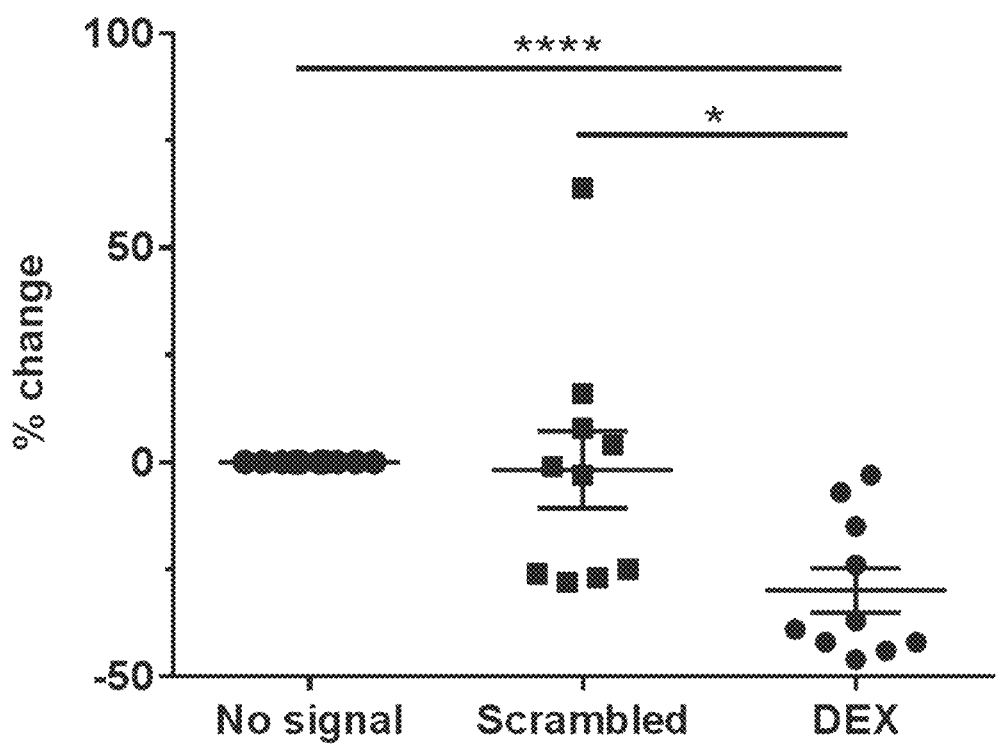
FIG. 21. Suppression of inflammatory responses in endotoxemic mouse by acoustic stimulation using a dexamethasone-specific signal. Three groups of mice were subjected to acoustic stimulation (no stimulation, scrambled dexamethasone signal, or dexamethasone signal). Animals were subjected to acoustic stimulation once per day for 6 days. Animals were challenged with endotoxin after 30 min. Circulating TNF levels were analyzed 90 min post-endotoxin. The TNF response was suppressed by acoustic stimulation using a dexamethasone-specific signal. n=10 mice/group, $*p<0.05$, $****p<0.0001$.

Different (naïve) mice were exposed to acoustic stimulation using the dexamethasone-specific or scrambled signal prior to intraperitoneal (i.p.) administration of lipopolysaccharides (LPS). Animals were subjected to acoustic stimulation once per day for 6 days. Animals were challenged with i.p. administration of endotoxin after 30 min. Circulating tumor necrosis factor (TNF) levels were analyzed 90 min after the endotoxin injection (FIG. 20). Acoustic stimulation using the dexamethasone-specific signal suppressed the inflammatory response induced by LPS administration (FIG. 21).

REFERENCES

1. Blalock J E (1984) The immune system as a sensory organ. *J Immunol* 132(3):1067-70.
2. Tracey K (2002) The inflammatory reflex. *Nature* 420 (6917):853-859.
3. Rosas-Ballina M et al. (2011) Acetylcholine-synthesizing T cells relay neural signals in a vagus nerve circuit. *Science* 334(6052):98-101.
4. Reardon C et al. (2013) Lymphocyte-derived ACh regulates local innate but not adaptive immunity. *Proc Natl Acad Sci USA* 110(4): 1410-1415.
5. Niijima A, Hori T, Katafuchi T, Ichijo T (1995) The effect of interleukin-1 beta on the efferent activity of the vagus nerve to the thymus. *J Auton Nerv Syst* 54(2): 137-144.
6. Niijima A (1996) The afferent discharges from sensors for interleukin 1 beta in the hepatoportal system in the anesthetized rat. *J Auton Nerv Syst* 61(3):287-291.
7. Niijima A (1992) Electrophysiological study on the vagal innervation of the adrenal gland in the rat. *J Auton Nerv Syst* 41(1-2):87-92.
8. Hansen M, O'Connor K, Goehler L, Watkins L, Maier S (2001) The contribution of the vagus nerve in interleukin-1beta-induced fever is dependent on dose. *Am J Physiol Regul Integr Comp Physiol* 280(4):R929-934.
9. Watkins L et al. (1995) Blockade of interleukin-1 induced hyperthermia by subdiaphragmatic vagotomy: evidence for vagal mediation of immune-brain communication. *Neurosci Lett* 183(1-2):27-31.
10. Czeschik J, Hagenacker T, Schäfers M, Büsselberg D (2008) TNF-α differentially modulates ion channels of nociceptive neurons. *Neurosci Lett* 434(3):293-298.
11. Hagenacker T, Czeschik J, Schäfers M, Büsselberg D (2010) Sensitization of voltage activated calcium channel currents for capsaicin in nociceptive neurons by tumor-necrosis-factor-α. *Brain Res Bull* 81(1):157-163.
12. Binshtok A et al. (2008) Nociceptors are interleukin-1beta sensors. *J Neurosci* 28(52):14062-14073.
13. Chiu I et al. (2013) Bacteria activate sensory neurons that modulate pain and inflammation. *Nature* 501(7465): 52-57.
14. Buzsáki G, Moser E I (2013) Memory, navigation and theta rhythm in the hippocampal-entorhinal system. *Nat Neurosci* 16(2): 130-138.
15. Nácher V, Ledberg A, Deco G, Romo R (2013) Coherent delta-band oscillations between cortical areas correlate with decision making. *Proc Natl Acad Sci USA* 110(37): 15085-15090.
16. Kopell N, Kramer M A, Malerba P, Whittington M A (2010) Are different rhythms good for different functions? *Front Hum Neurosci* 4:187.doi: 10.3389/fn-hum.2010.00187.
17. Famm K, Litt B, Tracey K, Boyden E, Slaoui M (2013) Drug discovery: a jump-start for electroceuticals. *Nature* 496(7444):159-161.
18. Koopman F A et al. (2012) Pilot study of stimulation of the cholinergic anti-inflammatory pathway with an implantable vagus nerve stimulation device in patients with rheumatoid arthritis. *Arthritis Rheum* 64(10 Suppl):S 195.
19. Kagan B L, Baldwin R L, Munoz D, Wisnieski B J (1992) Formation of ion-permeable channels by tumor necrosis factor-alpha. *Science* 255(5050): 1427-1430.
20. Heffner, H E and Heffner R S (2007) Hearing ranges of laboratory animals. *J Am Assoc Lab Animal Sci* 46(1): 11-13.
21. Heffner, H E and Heffner R S (1983) The hearing ability of horses. *Equine Practice* 5(3): 27-32.

What is claimed is:

1. A method for treating a first subject having a disease or disorder comprising administering to the first subject to be treated an acoustic playback of a previously recorded neurogram, the previously recorded neurogram being previously recorded from a second subject comprising a disease-specific neurogram or a condition-specific neurogram or an endogenous mediator-specific neurogram or a pharmacologic agent-specific neurogram, wherein the acoustic playback of the previously recorded neurogram is at an intensity and for a duration to treat the disease or disorder, and wherein the acoustic playback of the previously recorded neurogram is administered to the first subject via audio output.

2. The method of claim 1, wherein the disease or disorder is one or more of inflammation, type 1 diabetes, type 2 diabetes, metabolic syndrome, insulin resistance, glucose intolerance, hyperglycemia, hypoglycemia, trauma, bleeding, hemorrhagic shock, ischemia-reperfusion injury, nausea, vomiting, cancer, prostate cancer, arthritis, rheumatoid arthritis, sepsis, endotoxemia, colitis, pancreatitis, inflammatory bowel disease, Crohn's Disease, fever, anorexia, pain, swelling, kidney failure, liver disease, hypothyroidism, a host response to infection, an immune response, and a disease or disorder in which it is desirable to increase the activity or level of a cytokine.

3. The method of claim 1, wherein the second subject is an animal or a human having the disease, condition, endogenous mediator or pharmacologic agent at a time of recording the previously recorded neurogram.

4. The method of claim 1, wherein the previously recorded neurogram is obtained from a parasympathetic nerve, a sympathetic nerve, a cranial nerve or a somatic nerve of the second subject.

5. The method of claim 1, wherein the previously recorded neurogram is obtained from a vagus nerve, splenic nerve, splanchnic nerve, sciatic nerve, or a nerve to an organ or portion of an organ of the second subject.

6. The method of claim 1, wherein the previously recorded neurogram is used to modulate a cytokine-specific physiological effect.

7. The method of claim 1, wherein blood glucose levels are increased in the first subject when the first subject is being treated by the acoustic playback having the previously recorded neurogram comprising a hypoglycemia-specific, insulin-specific or cortisol-specific neurogram previously recorded from a vagus nerve of the second subject.

8. The method of claim 7, wherein the first subject receiving the acoustic playback of the previously recorded neurogram has one or more of hypoglycemia, kidney failure, liver disease and hypothyroidism.

9. The method of claim 1, wherein blood glucose levels are decreased in the first subject when the first subject is being treated by the acoustic playback having the previously recorded neurogram comprising a hyperglycemia-specific or glucose-specific neurogram previously recorded from a vagus nerve of the second subject.

10. The method of claim 9, wherein the first subject receiving the acoustic playback of the previously recorded neurogram has one or more of diabetes mellitus type 1, diabetes mellitus type 2, metabolic syndrome, insulin resistance, glucose intolerance and hyperglycemia.

11. The method of claim 1, wherein the disease or disorder of the first subject comprises inflammation and the inflammation is treated by acoustic playback to the first subject when the previously recorded neurogram is an anti-inflammatory-specific neurogram previously recorded from the vagus nerve of the second subject.

12. The method of claim 11, wherein the anti-inflammatory-specific neurogram is a dexamethosone-specific neurogram or a cortisol-specific neurogram.

13. The method of claim 1, wherein the previously recorded neurogram is obtained using implantable electrodes.

14. The method of claim 1, wherein the first subject receiving the acoustic playback of the previously recorded neurogram is a human.

15. The method of claim 1, wherein the acoustic playback of the previously recorded neurogram is applied to one or both ears of the first subject.

16. The method of claim 1, wherein the previously recorded neurogram is recorded from the second subject when the second subject has the disease or condition comprising hyperglycemia, hypoglycemia, euglycemic or inflammation.

17. The method of claim 1, wherein the previously recorded neurogram is recorded from the second subject when the second subject has the disease or condition comprising type 1 diabetes, type 2 diabetes, metabolic syndrome, insulin resistance, glucose intolerance, trauma, bleeding, hemorrhagic shock, ischemia-reperfusion injury, nausea, vomiting, cancer, prostate cancer, arthritis, rheumatoid arthritis, sepsis, endotoxemia, colitis, pancreatitis, inflammatory bowel disease, Crohn's Disease, fever, anorexia, pain, swelling, kidney failure, liver disease, hypothyroidism, a host response to infection, an immune response, or a disease or disorder in which it is desirable to increase the activity or level of a cytokine.

18. The method of claim 1, wherein the previously recorded neurogram is recorded from the second from the first subject in response to administration of the endogenous mediator or the pharmacological agent comprising a cytokine, a hormone or a metabolite.

19. The method of claim 1, wherein the previously recorded neurogram is recorded from the second subject in response to administration of the endogenous mediator or the pharmacological agent comprising glucose, glucagon, insulin, cortisol, dexamethasone, a chemokine, a colony stimulating factor, high-mobility group protein B1 (HMGB1), an interferon (IFN), an interleukin (IL), a tumor necrosis factor (TNF), TNFα, TNFβ, a lymphokine, macrophage migration inhibitory factor (MIF), a monokine, or a transforming growth factor beta (TGF-β).

20. The method of claim 19, wherein the interleukin is IL-1β or one or more of IL-1 through IL-36.

* * * * *